United States Patent [19]

Ruggio

[11] Patent Number: 5,476,450
[45] Date of Patent: Dec. 19, 1995

[54] APPARATUS AND METHOD FOR ASPIRATING INTRAVASCULAR, PULMONARY AND CARDIAC OBSTRUCTIONS

[76] Inventor: Joseph M. Ruggio, 27632 Fargo Rd., Laguna Hills, Calif. 92653-7808

[21] Appl. No.: 177,852

[22] Filed: Jan. 5, 1994

Related U.S. Application Data

[63] Continuation-in-part of Ser. No. 148,156, Nov. 4, 1993, abandoned.

[51] Int. Cl.$^6$ ................................................. A61M 25/01
[52] U.S. Cl. ........................... 604/93; 604/35; 604/104; 604/164; 606/128; 606/159; 606/194
[58] Field of Search ........................... 604/35, 43, 118, 604/119, 96, 22, 53, 93, 104, 164, 171; 606/170, 180, 159, 171, 128, 194; 128/768, 772, 662.06, DIG. 3

[56] References Cited

U.S. PATENT DOCUMENTS

| | | |
|---|---|---|
| 4,445,509 | 5/1984 | Auth . |
| 4,631,052 | 12/1986 | Kensey . |
| 4,692,139 | 9/1987 | Stiles . |
| 4,728,319 | 3/1988 | Masch . |
| 4,749,376 | 6/1988 | Kensey et al. . |
| 4,784,636 | 11/1988 | Rydell . |
| 4,790,812 | 12/1988 | Hawkins, Jr. et al. . |
| 4,968,307 | 11/1990 | Dake et al. . |
| 5,011,488 | 4/1991 | Ginsburg . |
| 5,090,960 | 2/1992 | Don Michael . |
| 5,163,905 | 11/1992 | Don Michael . |
| 5,176,693 | 1/1993 | Pannek, Jr. . |
| 5,181,920 | 1/1993 | Mueller et al. . |
| 5,273,526 | 12/1993 | Dance et al. . |
| 5,318,576 | 6/1994 | Plassche, Jr. et al. . |

FOREIGN PATENT DOCUMENTS

| | | |
|---|---|---|
| 0175096 | 7/1985 | European Pat. Off. . |
| 0314896 | 9/1988 | European Pat. Off. . |
| 0554616A3 | 11/1992 | European Pat. Off. . |

| | | |
|---|---|---|
| WO92/10971 | 12/1991 | WIPO . |

OTHER PUBLICATIONS

*Annals of Surgery*, Dec. 1971, vol. 174, No. 6, Transvenous Pulmonary Embolectomy by Catheter Device, Lazab J. Greenfield, M.D., Thomas A. Bauce, M.D., Ned B. Nichols, M.D., pp. 881–886.

*Asn. Surg.*, Oct. 1974, Transvenous Management of Pulmonary Embolic Disease, Lazar J. Greenfield, M.D., Marvin D. Peyton, M.D., Phillip P. Brown, M.D., Ronald C. Elkins, M.D., pp. 461–467.

*The Journal of Thoracic and Cardiovascular Surgery*, Dec., 1971, vol. 62, No. 6, Hemodynamic and Respiratory Responses to Transvenous Pulmonary Embolectomy, pp. 890–897.

Medi Tech Division–Instructions–Transvenous Pulmonary Embolectomy VB/10/100 Catheter Greenfield Pulmonary Embolectomy System (in 2 pages).

(List continued on next page.)

Primary Examiner—C. Fred Rosenbaum
Assistant Examiner—Perry E. Van Over
Attorney, Agent, or Firm—Knobbe, Martens, Olson & Bear

[57] ABSTRACT

Disclosed is an apparatus and technique for aspirating substances partially or completely occluding blood vessels or chambers of the heart. The aspirator assembly comprises a catheter assembly and a suction member for aspirating substances through the catheter. The catheter assembly comprises a catheter which travels over a guidewire. Exemplary suction members used for aspirating include a syringe or a vacuum reservoir. The method of treating the intravascular site comprises the steps of advancing a catheter assembly through a patient's vasculature until a distal end of the catheter assembly reaches an area close to the site, and aspirating occluding substances in the vicinity of the site through the distal end of the catheter assembly. The method may also include the additional steps of introducing medication through the catheter, and pulverizing the occlusion or any of its residue, prior to aspirating the occluding substances.

13 Claims, 13 Drawing Sheets

OTHER PUBLICATIONS

Hospital Practice, Jun. 15, 1992, Thrombolytic Therapy: A State of the Art Review, Claude R. Benedict, Susan Mueller, H. Vernon Anderson and James T. Willerson, pp. 43–54.

Chest, Dec. 1990, A Randomized Trial of a Single Bolus Dosage Regimen of Recombinant Tissue Plasminogen Activator in Patients with Acute Pulmonary Embolism, Mark Levine, M.D., Jack Hirsch, M.D., Jeff Weitz, M.D., Moira Cruickshank, M.D., Jean Neemeh, M.D., Alexander G. Turpie, M.B., Ch.B.; and Michael Gent, M.SC., pp. 1473–1479.

Radiology, Feb. 1990, Pulmonary Embolism: Segmental Appearance of Perfusion Lung Scan Defects Correlates with Successful Response to Thrombolytic Therapy, J. Anthony Parker, M.D., Stevan Nagel, M.D., David E. Drum, M.D., Sabah S. Tumeh, M.D., Samuel Z. Goldhaber, M.D., pp. 483–486.

Chest, Apr. 1992, Pulmonary Physiology During Pulmonary Embolism, C. Gregory Elliott, M.D., F.C.C.P., pp. 163S–171S.

Chest, Mar. 1993, Thrombotic Lesions in Primary Plexogenic Arteriopathy, C. A. Wagenvoort, M.D. and Paul G. H. Mulder, M.SC., pp. 844–849.

Chest, Mar. 1990, Natural Course of Treated Pulmonary Embolism, Renato Prediletto, M.D., Paolo Paoletti, M.D., Edo Fornai, B.S., Armando Perissinotto, B.S., Stefano Petruzzelli, M.D., Bruno Formichi, M.D., Stefano Ruschi, M.D., Antonio Palla, M.D., Antonio Giannella–Neto, Ph.D., and Carlo Guintini, M.D., pp. 554–561.

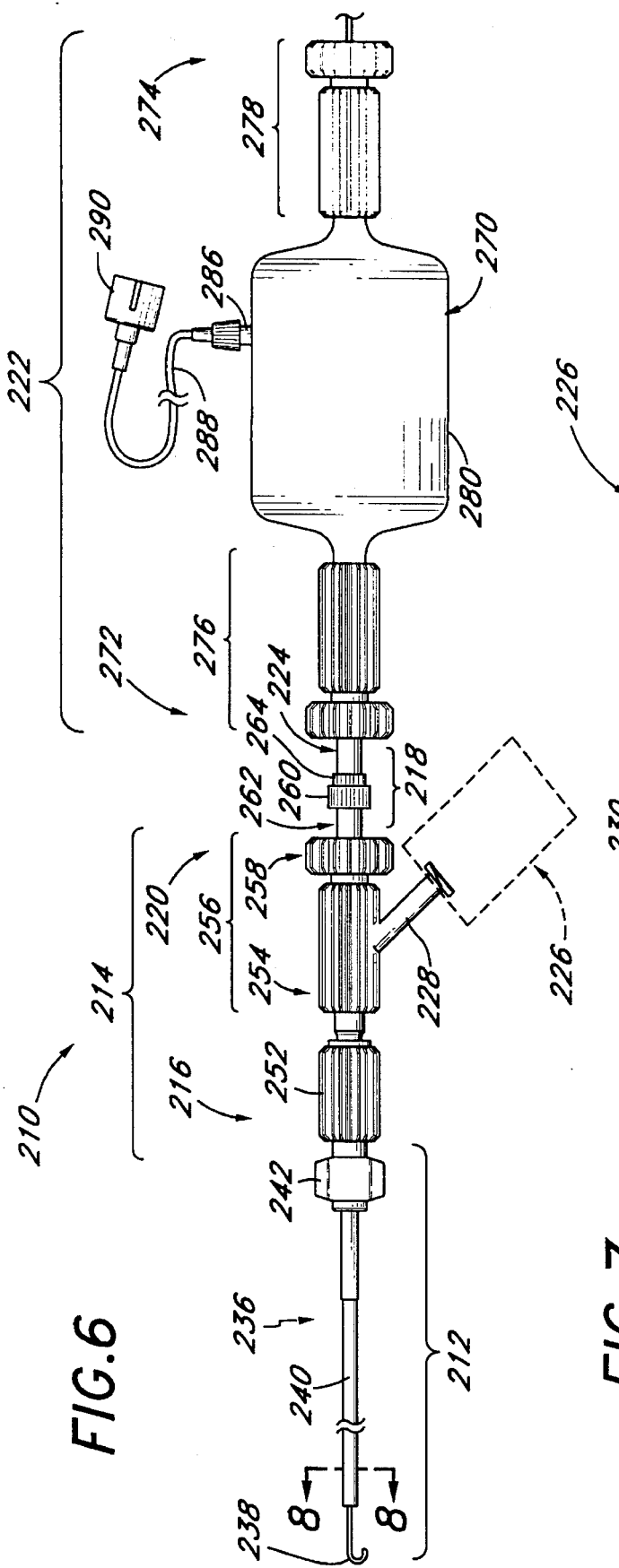
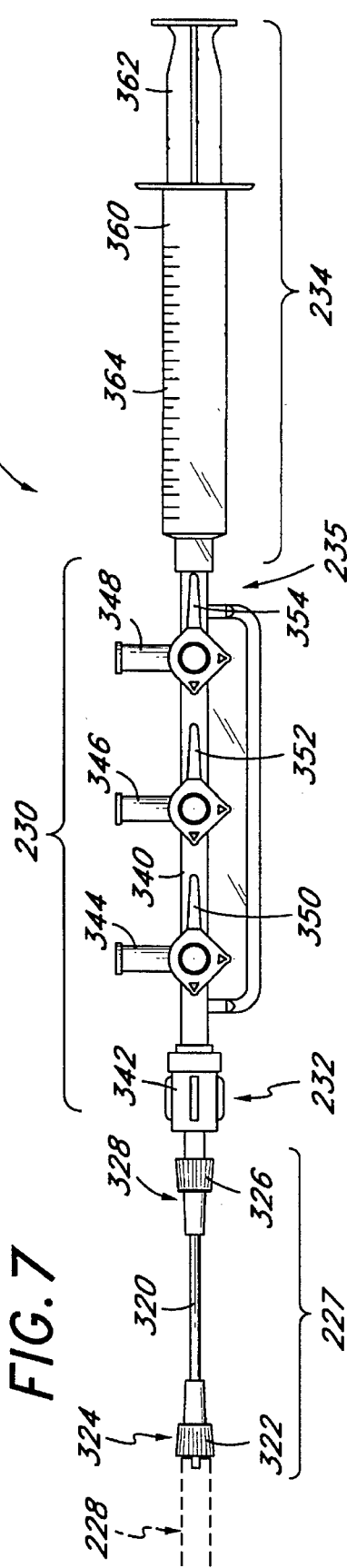
FIG.6
FIG.7

APPARATUS AND METHOD FOR ASPIRATING INTRAVASCULAR, PULMONARY AND CARDIAC OBSTRUCTIONS

CROSS REFERENCE TO RELATED APPLICATION

This application is a continuation-in-part to U.S. patent application Ser. No. 08/148,156, filed Nov. 4 1993, now abandoned by the same inventor, the disclosure of which is incorporated herein.

BACKGROUND OF THE INVENTION

1. Field of the Invention

The present invention relates to an apparatus and method for aspirating substances partially or completely obstructing blood vessels or the chambers of the heart.

2. Description of the Prior Art

Partial or complete obstruction of blood vessels or the chambers of the heart can result in serious morbidity or mortality. Such obstructions may result from emboli or thrombi, including clots formed from varying degrees of platelets, fibrin and cellular debris, products and components of the coagulation system and cholesterol, triglycerides and other fats.

One particularly devastating form of occlusion is pulmonary embolism. Risk factors for pulmonary emboli include fractures of or other injuries to the lower extremities, deep vein thrombosis of the lower extremities and pelvis, prolonged bed rest, obesity and hyper coagulable states. In pulmonary embolism, the emboli flow freely through the circulatory system until they flow into a pulmonary blood vessel which is small enough that they become lodged in the vessel, usually blocking blood flow. Pulmonary embolism results in complete or partial obstruction of the pulmonary arterial blood flow to the lung. This obstruction leads to a reduction in the cross-sectional area of the pulmonary arterial bed, and acutely can cause varying degrees of hypoxemia and circulatory compromise. The resulting loss of vascular capacity increases the resistance to pulmonary blood flow, which, if marked and persistent, leads to pulmonary hypertension and acute failure of the right ventricle.

At present, the most common treatment for pulmonary embolism is prevention. Several techniques exist for identifying the patient at high risk of death from this disease and prompt treatment following diagnosis is generally implemented to limit the frequency of embolism. However, ninety percent of the deaths from pulmonary emboli occur within the first two hours after embolization. Currently, there exists no effective technique or therapy which can be implemented within this time frame. This is because clinical diagnosis of pulmonary embolism is difficult. It is frequently present without clinical symptoms, for instance, pain or swelling, and it is absent in some 50% of patients in whom clinical symptoms suggest its presence. Furthermore, extensive thrombi can develop within minutes, resulting in extensive luminal occlusion. Present therapies and techniques are insufficient for interventional purposes in these cases. Accordingly, there exists a need for a technique of rapid and safe removal of occlusions from the intravascular system, including the pulmonary circulation and the coronary circulation, or the heart chambers.

Various therapeutic techniques exist for fragmenting or dissolving occluding substances. These techniques include the administration of clot/thrombus-dissolving drugs, balloon angioplasty, laser techniques, or mechanical fragmentation of the offending substances, with or without the adjunctive placement of stents.

Drugs which dissolve products of the coagulation system are referred to as "thrombolytic drugs," "thrombolytic agents" or simply "thrombolytics." There are four thrombolytics currently in use: streptokinase, urokinase, tissue plasminogen activator (tPA) and eminase. These drugs act to dissolve certain components of clots, effectively breaking up the clots into smaller pieces.

Although experience with thrombolytics indicates that they reduce in-hospital mortality rates from acute myocardial infarction, with pulmonary embolism, clots broken up by thrombolytics are often still large enough that they occlude vessels downstream, resulting in persistent hypoxemia and ultimately, the death of tissue, commonly known as infarction. Accordingly, there exists a need for the effective fragmentation of the residue of clots following the administration of thrombolytics in the treatment of partially or completely occluded vessels or heart chambers.

There is a myriad of catheter designs for treating intravascular or intracardiac obstructions. For example, U.S. Pat. No. 5,087,244 to Wolinsky et al. discloses a catheter having a perforated inflatable balloon for expressing drugs to the vascular wall. U.S. Pat. No. 5,021,044 to Sharkawy discloses an infusion catheter having a plurality of effluent flow ports along its outer wall, each having a successively larger diameter in the distal direction.

U.S. Pat. No. 4,968,307 to Dake et al. discloses another catheter for infusion of therapeutic fluids, in which each effluent flow port through the wall of the catheter is placed in fluid communication with a fluid source by a flow passageway extending throughout the length of and within the wall of the catheter.

U.S. Pat. No. 5,026,384 to Farr et al. discloses a torque tube having a rotatable cutter device affixed to its distal end for use in cutting plaque in arterial walls. A source of vacuum is connected to the torque tube for extracting the dislodged cuttings from the patient's bloodstream.

Such conventional apparatus provide means for dilating a partially or completely occluded vessel, or means for fragmenting an obstruction, but once treatment is complete, substances previously blocking the vessels or heart chambers may embolize downstream, causing infarction. Alternatively, the fragmented residue may coalesce, causing restenosis or infarction. In addition, these apparatus are generally complicated and difficult to operate, and have proven to be ineffective in the treatment of critical cases of pulmonary embolism, where time is of the essence.

For instance, the Farr device discloses the use of a torque tube having a cutter device affixed to its distal end, used for cutting plaque from artery walls. The operation of this device is not only difficult, as it involves the use of motorized rotating blades, but also dangerous, as the use of rotatable blades increases the risk of injury. In addition, the Farr device is limited to use on thrombi, which are obstructions formed at an intravascular site. It cannot be used on emboli, which are obstructions, including clots, which are freely flowing in the circulatory system. This is because the cutting device has no means of capturing the freely flowing emboli so that the emboli can be cut, unless the emboli is already lodged in a vessel. However, where an emboli is lodged, using the cutting device may cause the emboli to be further embedded in vessels downstream, which may be too small for the Farr device to reach. Thus, any vacuum means attached to the Farr device would be ineffective for removing emboli, particularly in cases where emboli must be removed promptly and safely.

Thus, there remains a need to remove the residue of occluding substances like emboli, promptly and safely, to prevent such downstream embolization.

SUMMARY OF THE INVENTION

The present invention addresses the problems encountered by conventional techniques in the treatment of partially or completely occluded vessels or heart chambers by providing a technique for the quick and safe removal of occlusions in intravascular or cardiac sites. The present invention also provides a technique for manually pulverizing the occluding substances, which facilitates the aspiration of the occluding substances.

A first aspect of the present invention is an apparatus for removing emboli from an intravascular site. The apparatus comprises a guide having an elongated tubular body and a suction member connected to the guide for aspirating the emboli through the elongated tubular body of the guide. In a preferred embodiment, the apparatus includes a guidewire, which is inserted into the guide. In another preferred embodiment, the suction member is a syringe or a vacuum reservoir. In yet another embodiment, the apparatus includes a manifold. The manifold comprises a tubular member having a first end and a second end, at least one port with a control valve and a rotatable hub mounted on the first end of the tubular member. The hub has internal threads for engagement with the guide. In addition, the second end of the manifold is connected to a syringe. In other preferred embodiments, the intravascular site is a pulmonary site or a cardiac site.

A second aspect of the present invention is a method of removing free emboli from an intravascular site. The method comprises the steps of: advancing a catheter through a patient's vasculature until a distal end of the catheter extends into an area close to the site; introducing a medication through a proximal end of the catheter to discharge the medication through the distal end of the catheter; and aspirating occlusions in the vicinity of the site through the distal end of the catheter, without cutting the emboli from the site. In accordance with a preferred method of removing free emboli from an intravascular site, the catheter is advanced over a guidewire prior to advancing the catheter through the patient's vasculature. In accordance with another preferred method of removing free emboli, the intravascular site includes a pulmonary site. In yet another preferred method of removing free emboli, the intravascular site includes a cardiac site.

A further aspect of the present invention is a method of treating a pulmonary site. The method comprises the steps of: advancing a catheter assembly through a patient's vasculature until a distal end of the catheter assembly extends into an area close to the site, and aspirating occlusions in the vicinity of the site through the distal end of the catheter. The catheter assembly comprises a catheter traveling over a guidewire.

Yet another aspect of the present invention comprises a method of treating an intravascular site, comprising the steps of: advancing a catheter through a patient's vasculature until a distal end of the catheter extends into an area close to the site; and pulverizing occlusions in the vicinity of the site by means of a guidewire. In accordance with a preferred embodiment of the present invention, the method of treating an intravascular site further includes the step of introducing a medication through a proximal end of the catheter to discharge the medication through the distal end of the catheter, prior to pulverizing the occlusions. In accordance with another preferred embodiment, the method further includes the step of aspirating occlusions in the vicinity of the site through the distal end of the catheter, after pulverizing the occlusions with a guidewire. In accordance with a further preferred embodiment, the method includes the step of advancing the catheter over a guidewire prior to advancing the catheter through the patient's vasculature.

A further aspect of the present invention comprises an improved apparatus for removing intravascular occlusions. The apparatus comprises a catheter having an elongated tubular body with at least a first lumen extending therethrough, a proximal end and a distal end; an infusion wire comprising an elongated tubular body, a proximal end and a distal end, and a tip having a cap which defines an aperture; and a suction member coupled to the catheter for aspirating occlusions at the distal end of the catheter through the elongated tubular body of the catheter. In a preferred embodiment, the aperture on the cap is located along a side wall of the tip. In another embodiment, the aperture is located substantially at an apex of the cap. In yet another embodiment, the infusion wire additionally comprises a guidewire. In a further embodiment, the guidewire comprises at least one strut. In other preferred embodiments, the intravascular site is a cardiac site or a pulmonary site.

Another aspect of the present invention is a method of removing occlusions from an intravascular site. The method comprises the following steps: first, a catheter assembly is advanced through a patient's vasculature until a distal end of the catheter assembly extends into an area close to the site. This catheter assembly comprises a catheter having an elongated tubular body with a first lumen and a second lumen extending therethrough, a distal end and a proximal end; and a guiding structure inserted within the first or the second lumen, for directing the catheter to the intravascular site. The guiding structure is then removed from the catheter assembly. An infusion wire is next inserted into the catheter. This infusion wire comprises an elongated tubular body, a proximal end and a distal end, a tip having a cap which defines an aperture located at substantially the apex of the cap, and a guidewire inserted within the elongated tubular body and through the aperture. A medication is then introduced through the proximal end of the infusion wire to discharge the medication through the distal end of the infusion wire. Occlusions are then aspirated through the first or second lumen of the catheter. In a preferred embodiment, occlusions may be pulverized with the tip of the infusion wire.

An additional aspect of the present invention is a method of removing occlusions from an intravascular site, comprising the steps of: advancing a catheter through a patient's vasculature until a distal end of the catheter extends into an area close to the site, advancing a hollow tube within the catheter until a distal end of the tube extends into an area close to the site, and aspirating the occlusions through the hollow tube. In a preferred embodiment, the intravascular site is a pulmonary site. In a second embodiment, the intravascular site is a cardiac site.

BRIEF DESCRIPTION OF THE DRAWINGS

FIG. 6 is an elevation view of a preferred embodiment of an improved aspirator assembly for use in the method of the present invention;

FIG. 7 is an elevation view of the infusion assembly used in the improved aspirator assembly of FIG. 6;

FIG. 11b is a cross-section view of the infusion wire along lines 11b—11b of FIG. 11a;

FIG. 12b illustrates a cross-section view of the infusion wire along lines 12b—12b of FIG. 12a;

DETAILED DESCRIPTION OF THE PREFERRED EMBODIMENTS

The present invention addresses the problems encountered by conventional techniques in the treatment of partially or completely occluded vessels or heart chambers by utilizing an apparatus and technique for manually pulverizing the occluding substances and aspirating the occluding substances.

Figure 1:
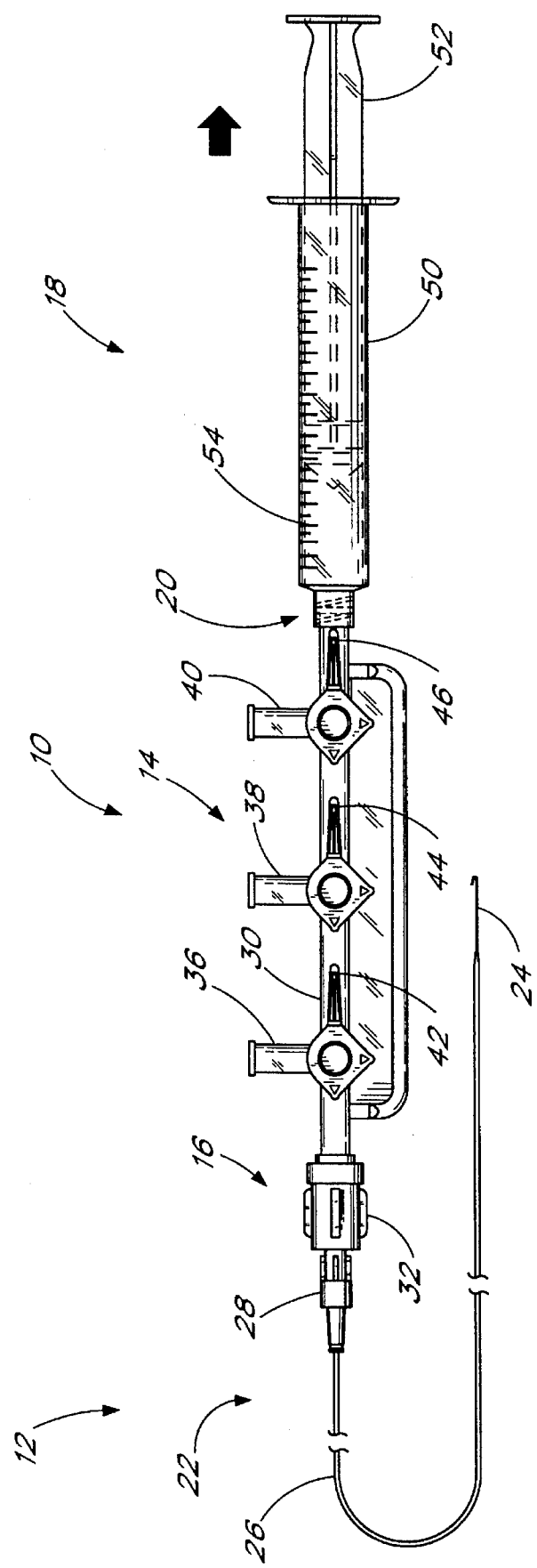
FIG. 1 is an elevation view of a preferred embodiment of the aspirator assembly used in the method of the present invention.

FIG. 1 illustrates one embodiment of the aspirator assembly 10 used in the method of the present invention. The aspirator assembly 10 comprises a catheter assembly 12, a manifold 14 connected to the catheter assembly 12 at a first end 16 and a syringe 18 connected to the manifold 14 at a second end 20 of the manifold 14.

The catheter assembly 12 is conventional, and comprises a catheter 22 which travels over a steerable guidewire 24, as is known in the art. The catheter 22 comprises an elongated, flexible tube 26 attached to a connector 28. Advantageously, a conventional multipurpose catheter may be used. Guidewires are commercially available in a variety of sizes and with a variety of tips. An exemplary guidewire comprises a 0.035-inch or a 0.038-inch diameter guidewire with a J-tip or a straight tip. Such catheter assemblies are available from Cordis Corporation, located in Miami, Fla.

The manifold 14 is conventional. An exemplary manifold 14 is depicted in FIG. 1 and comprises a tubular member 30 with a hub 32 mounted over one end 16 of the tubular member 30, and three T-connectors 36, 38, 40, forming inlets or outlets located along the body of the tubular member 30. Associated with each T-connector 36, 38, 40 is a control valve 42, 44, 46. The hub 32 is freely rotatable around the longitudinal axis of the tubular member 30 and has internal threads (not shown) for engaging a connector 28 at one end of the catheter 22. Typical suppliers of the manifold include Merit Inc., which is located in Salt Lake City, Utah and Namic, which is located in Albany, N.Y.

Various fluids may be introduced through each T-connection 36, 38, 40 of the manifold 14. Some fluids used are: saline, which is used for flushing the catheter 22; a radiopaque contrast agent, which is used to determine the patency of the vessel or chamber under fluoroscopic examination, or for providing fluoroscopic guidance of the catheterization process; or any medication required. A control valve 42, 44, 46 is connected to each T-connector 36, 38, 40 and is used to regulate the amount of fluid required. One of the T-connectors 36, 38 or 40 may be connected to a source of vacuum.

In the present embodiment, a conventional syringe 18 is connected to the manifold 14, at the end 20 opposite to the hub 32. The syringe 18 comprises a generally tubular body 50 and a plunger 52. Markings 54 indicating the fluid capacity of the syringe 18 are located on the exterior wall of the tubular member 50. The syringe 18 is commercially available from Namic, located in Albany, N.Y. Advantageously, a vacuum reservoir (not shown) may be used in place of the syringe 18. Such vacuum reservoirs may take the form of vacuum bottles, which are known in the art. These vacuum bottles are available from Inter Ventional Technologies, Inc. of San Diego, Calif.

In addition, a pressure monitoring system (not shown) may be connected to the manifold 14 by at one of the T-connectors 36, 38 or 40, as known in the art. The pressure monitoring system is used to monitor pressure within the cardiac chambers and large vessels during catheterization, and it provides important information regarding hemodynamics, such as the flow and pressure of vessels and the heart chambers. In operation, the catheter assembly 12, the manifold 14 and the syringe 18 are all in fluid communication with one other.

Figure 2:
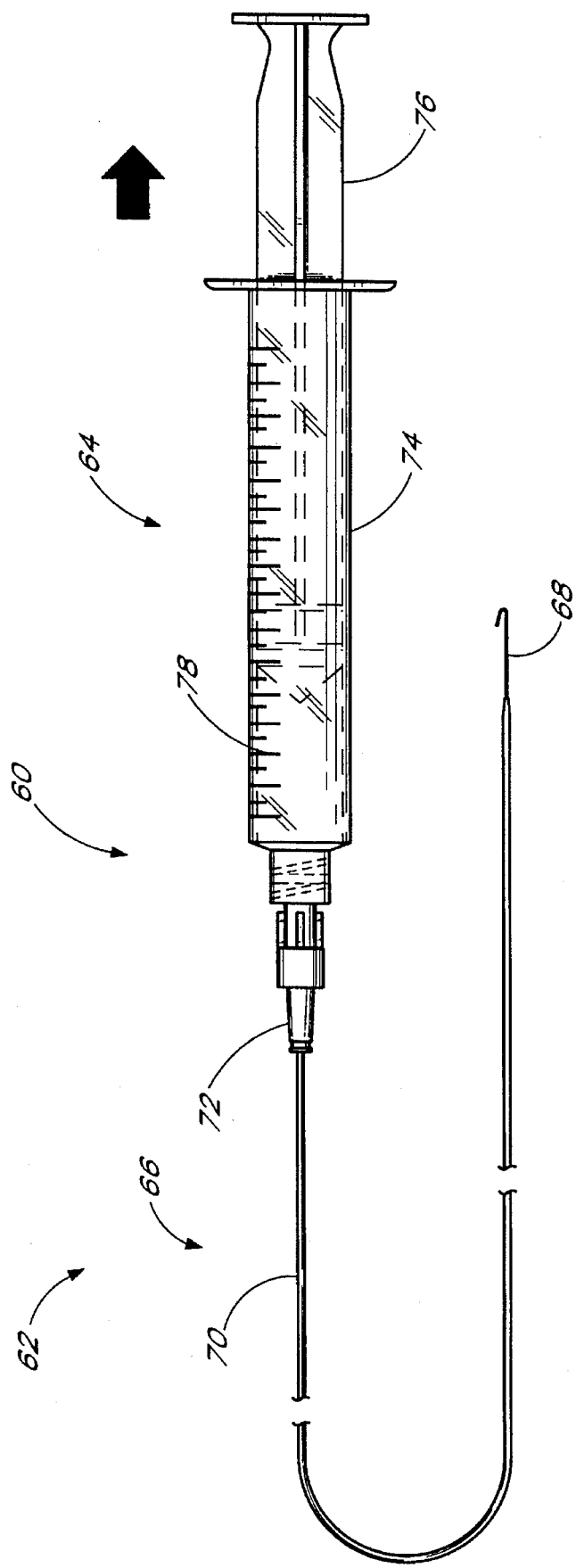
FIG. 2 is an elevation view of an alternative embodiment of the aspirator assembly for use in the method of the present invention.

FIG. 2 illustrates a second embodiment of the aspirator assembly 60 of the present invention. This embodiment of the aspirator assembly 60 comprises a catheter assembly 62 and a syringe 64 connected to the catheter assembly 62.

The catheter assembly 62 is conventional, and comprises a catheter 66 which travels over a steerable guidewire 68, as is known in the art. The catheter 66 comprises an elongated, flexible tube 70 attached to a connector 72. Alternatively, a conventional multipurpose catheter may be used. Guidewires are commercially available in a variety of sizes and with a variety of tips. An exemplary guidewire comprises a 0.035-inch or a 0.038-inch diameter guidewire with a J-tip or a straight tip. Such catheter assemblies are available from Cordis Corporation in Miami, Fla.

A conventional syringe 64 is connected to the connector 72 of the catheter 66. The syringe 64 comprises a generally tubular body 74 and a plunger 76. Markings 78 indicating the fluid capacity of the syringe 64 are located on the exterior wall of the tubular member 74. An exemplary syringes 64 is commercially available from Namic, which is located in Albany, N.Y. Advantageously, a vacuum reservoir (not shown) may be used in place of the syringe 64. Such vacuum reservoirs may take the form of vacuum bottles, which are known in the art. An exemplary vacuum bottle is available from Inter Ventional Technologies, Inc. in San Diego, Calif. In operation, the catheter assembly 62 and the syringe 64 are in fluid communication with one another.

Figure 3:
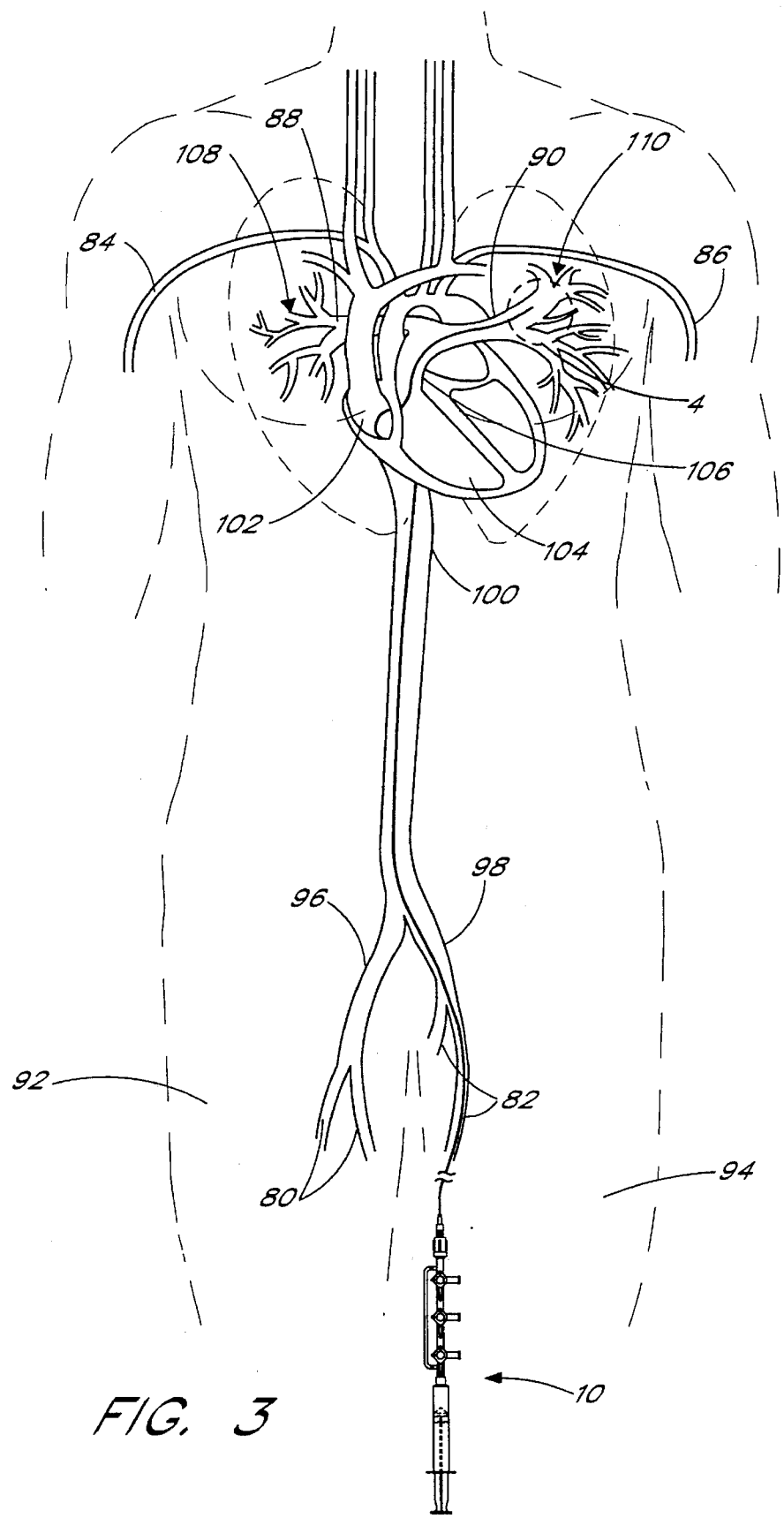
FIG. 3 illustrates the aspirator assembly of FIG. 1, with the catheter assembly advanced into a pulmonary artery of the human body through the femoral vein.

In use and as illustrated in FIG. 3, access to the intravascular system or heart chambers is generally gained through the right or left femoral artery (not shown) or vein 80, 82. Alternatively, access may also be gained through the brachial vessels 84, 86 in the right and left arms.

In treating pulmonary embolism, access to the main pulmonary arteries 88, 90 is generally made through the right or left femoral vein 80, 82 located in either the right or the left thigh 92, 94, as shown in FIG. 3. A Cook needle (not shown) is first used to puncture the vein 80 or 82. The Cook needle is commercially available from Cook Incorporated in Bloomington, Ind. In one embodiment, a conventional J-tipped guidewire (not shown) is then inserted into the needle into the artery or vein. The needle is then removed.

Next, a conventional sheath assembly (not shown) comprising a dilator and a sheath, is advanced over the J-tipped guidewire and inserted into the vein 80 or 82. As is known, such conventional sheath assemblies are generally equipped with a side arm for flushing. Once the sheath assembly is in place, the J-tipped guidewire and the dilator are removed and the sheath assembly is flushed with saline solution through the side arm of the sheath assembly. An appropriate catheter assembly 12, for example, a catheter 22 with a J-tipped guidewire 24 (see FIG. 1) or a straight tip guidewire (not shown), is then advanced through the sheath to the intravascular site or heart chamber under examination. The tip of the guidewire 24 is always advanced ahead of the elongated tube portion 26 of the catheter 22, to minimize any risk of damage to the walls of the blood vessel. In one embodiment, the catheter 22 may be advanced through the sheath to the intravascular site or heart chamber without the use of a guidewire 24. An exemplary catheter for such use is a conventional multipurpose catheter or a balloon-tipped catheter.

As depicted in FIGS. 1 and 3, to reach the main pulmonary arteries 88, 90, the catheter assembly 12 is first advanced up the femoral vein 80 or 82, with the connector 28 of the catheter assembly 12 remaining outside the vein 80 or 82. The catheter assembly 12 is then connected to the manifold 14 and the catheter assembly 12 is flushed vigorously. To flush the catheter assembly 12, the control valve 42, 44 or 46 regulating the flow of saline solution is opened. The required amount of saline is drawn into the syringe 18. Next, the valve 42, 44 or 46 is closed and the saline may then be injected into the vessel or chamber under treatment. Medication may also may administered in the same manner.

Under pressure monitoring and/or fluoroscopic guidance, the catheter assembly 12 is advanced through the right or left common iliac 96 or 98 and the inferior vena cava 100, into the right atrium 102. The catheter assembly 12 is then advanced through the tricuspid valve (not shown) into the right ventricle 104, up the pulmonary trunk 106, and henceforth into the right or left main pulmonary artery 88 or 90. Once the catheter assembly 12 reaches the pulmonary trunk 106, or the cardiac chambers 102, 104, a radiopaque contrast agent may be injected through the connector 28 of the catheter 22, to facilitate fluoroscopic guidance of the catheter assembly 12 into the pulmonary artery 88 or 90. Typical contrast agents used include ionic contrast agents such as Renograffin or MD 76, or nonionic contrast agents such as Optiray or Hexabrix. Renograffin is commercially available through Bristol-Myers Squibb Diagnostics in Princeton, N.J. MD 76, Optiray and Hexabrix are all commercially available from Mallinckrodt Incorporated in St. Louis, Mo.

Selective injection of the radiographic contrast agent into the cardiac chambers 102, 104, pulmonary trunk 106 or pulmonary vessels 88, 90, 108, 110 facilitates contrast radiographic inspection of the vessel, which in turn permits the placement of the catheter assembly 12 into the intravascular site of interest. A contrast agent is also injected into the site under examination during recording of radiographic images. Each vessel is usually viewed in several projections, to permit assessment of severity of stenosis or occlusive emboli and to minimize overlap of adjacent vessels. Injecting the contrast agent into the pulmonary system also facilitates the location of occlusions such as clots in the pulmonary vessels 108, 110.

Under fluoroscopic guidance, the catheter assembly 12 is advanced to the occluded pulmonary artery. Next, the guidewire 24 may be withdrawn from the catheter assembly 12 and treatment of the intravascular site in accordance with the present invention begins. The guidewire 24 may, however, be left in place during treatment.

Figure 4:
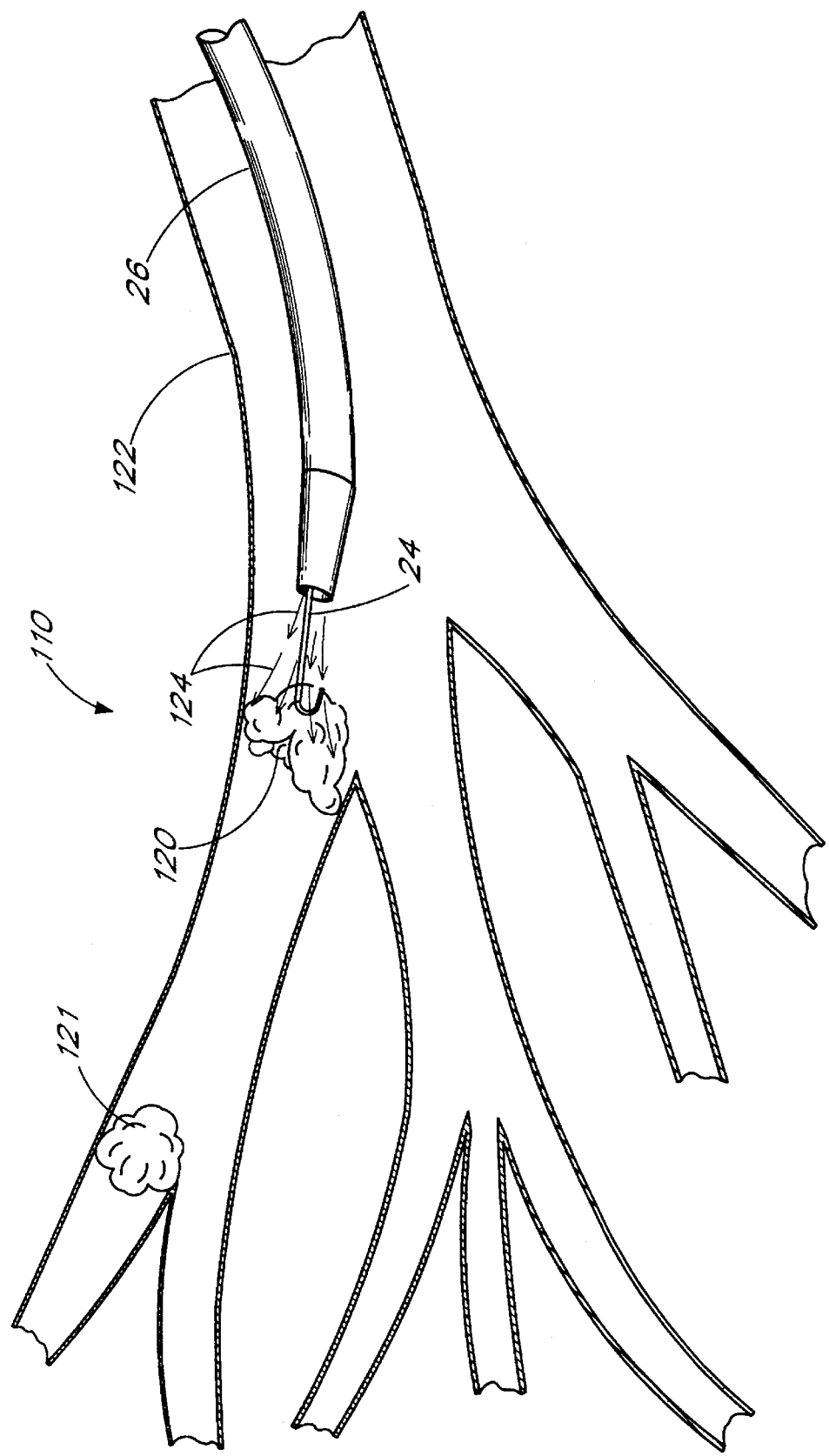
FIG. 4 illustrates an enlarged view of the catheter assembly along lines 4—4 of FIG. 3 being used to pulverize occlusions within a vessel.

As shown in FIG. 4, the elongated tube portion 26 of catheter 22 (or catheter assembly 12) is positioned close to the occlusion 120 in the pulmonary vessel 122 once the position of the occlusion 120 is determined. In the present embodiment, a thrombolytic agent is administered to the occlusion 120, as depicted by arrows 124 through the elongated tube 26 of catheter 22 via one of the T-connectors 36, 38 or 40 of the manifold 14. There are four thrombolytics currently in use: streptokinase, urokinase, tissue plasminogen activator (tPA) and eminase. These drugs act to dissolve certain components of clots, effectively breaking up the clots into smaller pieces. Streptokinase is commercially available through Astra Pharmaceutical Products, Inc. in Westboro, Mass.; urokinase is available through Abbott Laboratories in Chicago, Illinois; tPA is available through Genentech Inc. in San Francisco, Calif.; and eminase is available through Smithkline Beecham Pharmaceuticals in Philadelphia, Pa.

An anticoagulation agent such as Heparin may also be administered to the occlusion 120 to minimize coagulation of the occlusion 120 when it is fragmented. Heparin is commercially available through The Upjohn Company in Kalamazoo, Mich.

Figure 5:
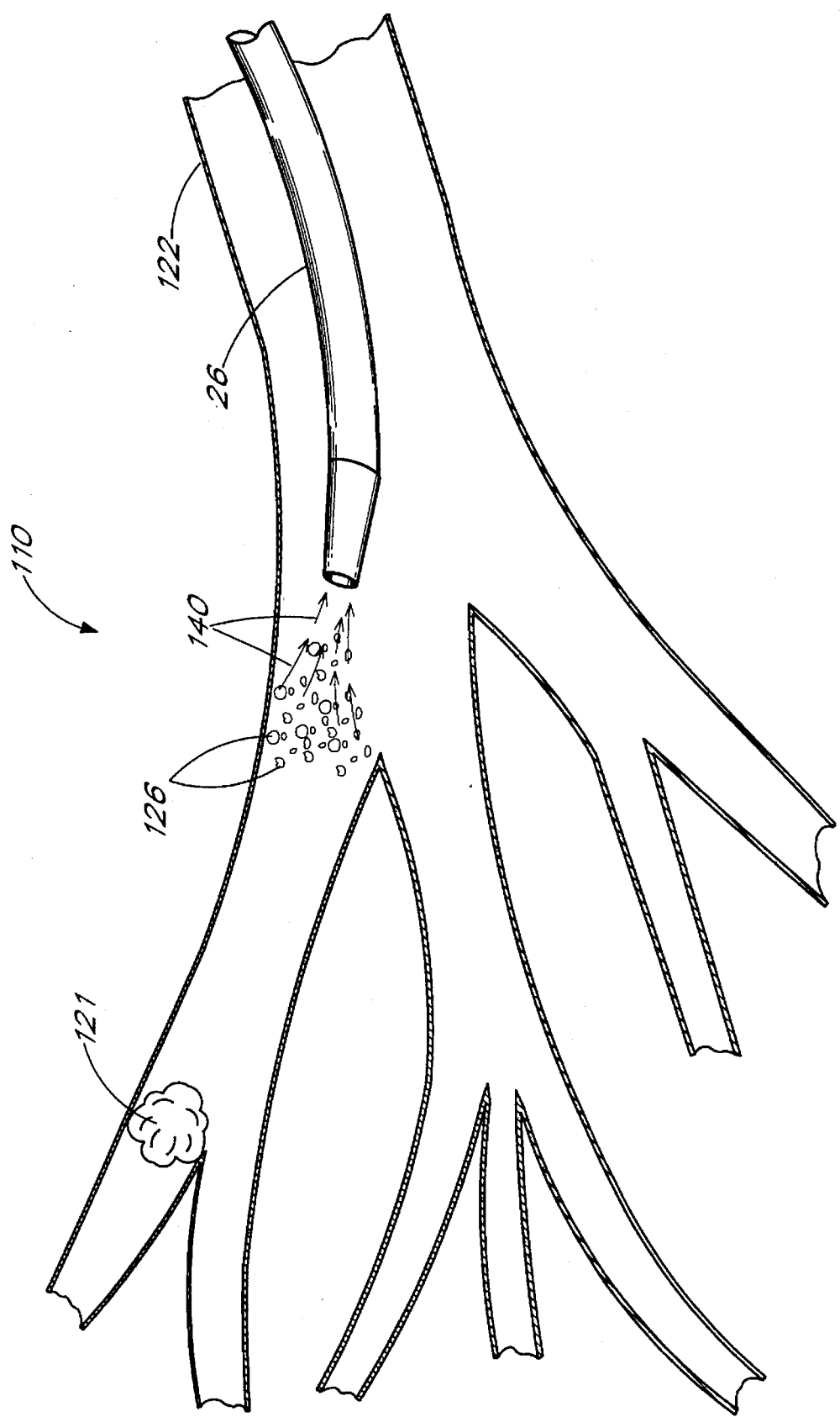
FIG. 5 illustrates the catheter assembly of FIG. 4 being used to aspirate occluding substances within a blood vessel.

If the thrombolytic agent acts sufficiently to break the occlusion 120 into small enough pieces, the residue 126 of the occlusion 120 is aspirated immediately by means of the syringe 18 or a vacuum reservoir, as depicted by the arrows 140 shown in FIG. 5. Aspiration of the residue 126 is accomplished by first placing the tip of the elongated tube 26 of catheter 22 close to the residue 126 of the occlusion 120 under fluoroscopic guidance. Next, the plunger 52 of the syringe 18 is drawn backwards, which creates a pressure difference within the tubular body 50 of the syringe 18. This pressure difference acts almost instantaneously to draw the residue 126 of the occlusion 120 into the syringe 18. Typically, a 50 cc syringe would be sufficient for this purpose. Alternatively, a vacuum reservoir (not shown) may be used in place of the syringe. The vacuum reservoir may be connected to the manifold 14 at one of the T-connectors 36, 38, 40 or at the end 20 opposite to the hub 32. An exemplary vacuum reservoir is a vacuum bottle. This procedure may be repeated as needed. When the occlusion 120 or its residue 126 has been removed, the elongated tube 26 of catheter 22 may be advanced under fluoroscopic guidance to vessels downstream, so that occlusions 121 further downstream may be similarly removed.

However, if the thrombolytic agent does not break the occlusion 120 into sufficiently small pieces for immediate aspiration through the catheter 22, the guidewire 24 in the catheter assembly 12 is used to manually pulverize the occlusion 120 or its residual pieces 126 into particles small enough to be aspirated, as shown in FIGS. 4 and 5. The catheter assembly 12 may first be disconnected from the manifold 14 prior to performing this procedure. If the guidewire 24 has been removed during the earlier part of the procedure, it may be reintroduced into the catheter 22 so that pulverization of the occlusion 120 may be performed. When the residue 126 has been pulverized into particles small enough to pass through the catheter 22, the plunger 52 of the syringe 18 is drawn backwards, drawing the residue 126 of the occlusion 120 into the syringe 18. The pressure within the patient's heart chambers or vessels is monitored throughout the above described procedure. When contrast radiographic inspection indicates that there is no evidence of any remaining residual occlusions 126, the catheter 22 or catheter assembly 12 is removed.

The present invention may also be performed using the aspirator assembly 60 illustrated in FIG. 2. Once the position of the occlusion 120 has been determined, the thrombolytic agent may be directly injected through the catheter 66 and into the vessel 122 by means of the syringe 64. Upon fragmentation, the residue 126 is immediately aspirated by drawing the plunger 76 of the syringe 64 backwards. As described above, the pressure difference created by drawing the plunger 76 backwards draws the residue 126 of the occlusion 120 into the syringe 64. As described above, a vacuum reservoir (not shown), such as a vacuum bottle, may be used in place of the syringe 64. Aspiration of the occluding substances 120 or 126 may be performed at any stage using the catheter 66 and syringe 64.

It should be noted that any occlusion within a vessel or any heart chamber may be aspirated in the manner described above without first administering thrombolytic agents if the occlusions are small enough to be aspirated. The above described procedure can be performed in any part of the intravascular, pulmonary or coronary system, or within the chambers of the heart.

Through practicing the present invention, occlusions which have advanced with blood flow into small vessels or heart chambers and which block such vessels or chambers may be successfully and permanently removed from the vessel or chamber, eliminating the risk of hypoxemia, circulatory compromise or infarction downstream.

In accordance with a further aspect of the present invention, there is disclosed an improved aspirator assembly. With reference to FIG. 6, the improved aspirator assembly 210 comprises a catheter assembly 212 connected to a y-connector 214 at the distal end 216 of the y-connector 214, a connector assembly 218 connected to the proximal end 220 of the y-connector 214 and an evacuation module 222 which is connected to the proximal end 224 of the connector assembly 218. The aspirator assembly 210 further comprises an infusion assembly 226 which is connected to a side arm 228 of the y-connector 214.

As illustrated in FIG. 7, the infusion assembly 226 comprises a connector assembly 227 connected to a side arm 228 of the y-connector 214, a manifold 230 connected to the connector assembly 228 at a distal end 232 of the manifold 230 and a syringe 234 connected to the proximal end 235 of the manifold 230.

With reference to FIG. 6, the catheter assembly 212 comprises a catheter 236 which travels over a steerable guidewire 238. Guidewires are commercially available in a variety of sizes and with a variety of tips. An exemplary guidewire comprises a 0.035-inch or a 0.038-inch diameter guidewire with a J-tip or a straight tip.

Figure 8A:
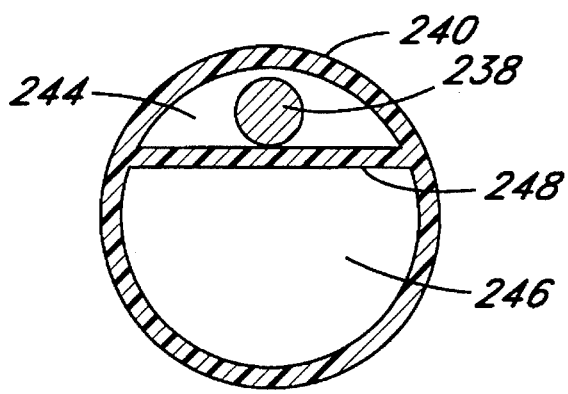
FIG. 8a illustrates a cross-section view of a preferred embodiment of the improved catheter assembly along lines 8—8 of FIG. 6.
Figure 8B:
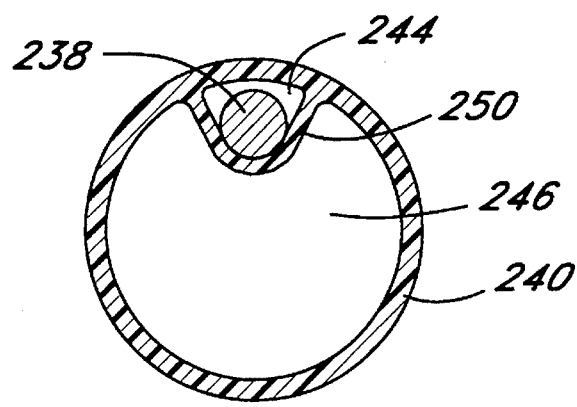
FIG. 8b illustrates a cross-section view of an alternate embodiment of the improved catheter assembly of FIG. 6.

The catheter 236 comprises an elongated, flexible tube 240 attached to a connector 242. Preferably, and as illustrated in FIG. 8a, the elongated tube 240 defines a first lumen 244 and a second lumen 246, which are separated by a partition 248. In one embodiment, the first lumen 244 has a smaller cross-sectional area than the second lumen 246. Alternatively, and as depicted in FIG. 8b, the partition 248 of the catheter 240 forms a groove 250. The first lumen 244 and groove 250 each provide a path through which the guidewire 238 may be advanced.

Preferably, catheter 236 is made of a material which is sufficiently strong to maintain the compressive forces exerted by intravascular walls through which the catheter 236 will be advanced. At the same time, the wall of the catheter 236 should be of a sufficiently thin construction so that lumen 246 will be provided with the largest possible cross-section for aspiration purposes. Catheter 236 is preferably also made from materials which have at least a biocompatible exterior surface.

Biocompatibility can be enhanced by applying any of a variety of coatings to the exterior wall of the catheter 236. In addition, other coatings which inhibit thrombus formation or which provide a smooth surface, may be used, as will be understood by one of skill in the art. The provision of a smooth coating on the exterior surface of catheter 236 serves, in part, to prevent scarring of the intravascular walls as the catheter 236 is advanced into the intravascular system.

In a preferred embodiment, both the interior and exterior surfaces of catheter 236 are coated to impart the properties discussed above. Alternatively, only the interior or exterior surface of catheter 236 alone could be coated, or multiple coats of the same or different material could be used on the interior or exterior surface of catheter 236.

Suitable coating materials such as polyethylene or PET or other materials can be readily selected by one of skill in the art. In general, any biocompatible material which can tolerate the compressive forces exerted by the intravascular walls can be used. However, a non-bio-compatible material may be used as one of multiple coatings where the non-biocompatible material is sandwiched between other layers, such that the material is not exposed to body tissues.

Coating material may be applied to individual surfaces by painting, bonding with a suitable adhesive or mechanically fixing as appropriate to the material of the coating and material comprising the bulk of the catheter body as will be appreciated by one with skill in the art. Alternatively, internal and external coatings may be applied by inserting the elongated tube 240 of the catheter 236 into an envelope of suitable material as discussed above.

The wall thickness of the catheter 236 will vary depending on the required application. The wall thickness of the catheter 236 should be sufficient to withstand radial, inwardly-directed forces exerted by the intravascular walls. However, the wall and the partition 248 or 250 should be sufficiently thin for a selected construction material to enable the catheter 236 to define sufficiently large lumens 244 and 246 for the insertion of a guidewire 238, or other guides, and for aspirating occlusions.

Typically, the wall thickness of catheter 236 made of latex is preferably between about 0.008 and 0.015 inches. More preferably, the catheter 236 has a wall thickness of between about 0.0095 and 0.013 inches. In some cases a wall thickness of less than about 0.008 inches may be desired. In addition, some instances may require a wall thickness of greater than about 0.015 inches.

Furthermore, the thickness of the partition 248 or 250 should preferably be between about 0.007 to 0.012 inches. More preferably, the catheter 236 should have a partition 248 or 250 thickness of between about 0.008 to 0.011 inches. As with the wall thickness, some cases may require a partition 248 or 250 thickness of less than about 0.007 inches. Likewise, some situations may call for a partition 248 or 250 thickness of greater than about 0.012 inches.

The wall thickness and partition 248 or 250 thickness will generally be substantially uniform throughout the axial length of the catheter 236. However, the wall thickness on the distal end of the catheter 236 may be different from the wall thickness on the medial portion of the catheter 236, such as in the case where the distal end of the catheter 236 is tapered, to effect the delivery of medication or aspiration of occlusions. In addition, the wall thickness on the distal end of the catheter 236 may be different from the wall thickness on the proximal end of the catheter 236, such as in the case where bonding to the connector 242 is required, so that the strength profile of the bond may be increased.

In addition, the tip of the catheter 236 may be configured in a variety of shapes, depending on the intended application. The catheter 236 may have a straight tip, an angled tip or a pig-tail tip, as is known in the art.

The outer diameter, axial length, lumen diameter and tip configuration of the catheter 236 will vary with the specific intended application. One skilled in the art will be readily able to choose the appropriate insertion diameter and the appropriate tip configuration of the catheter 236 depending on the diameter of the artery to be treated and the location of the treatment site.

Preferably, catheter 236 has an outer diameter of between about 0.079 inches (6 French) and 0.131 inches (10 French) for a catheter made of latex. Both ideal outer diameter and ideal wall thickness will be determined by the inherent strength of the material used and the size of the blood vessel to which the catheter 236 will be advanced, as is apparent to one skilled in the art. Therefore, the dimensions given herein should be considered exemplary.

Furthermore, the clinician should select a catheter 236 having an axial length that will be sufficiently long to traverse to the treatment site. The axial length of the catheter 236 for intravascular, pulmonary and cardiac applications will typically be in the range from about 40 inches to 50 inches. The axial length may vary considerably from case to case depending upon the application to different parts of the anatomy.

Figure 8C:
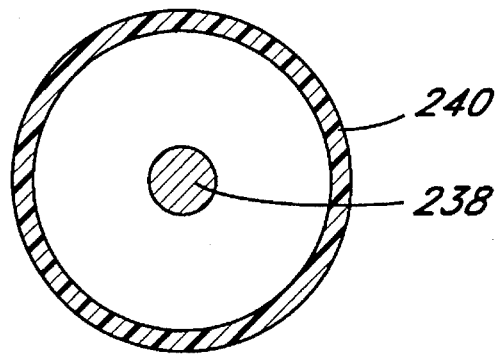
FIG. 8c illustrates a cross-section view of a further embodiment of the improved catheter assembly of FIG. 6.

In a further embodiment, a conventional single lumen catheter, as illustrated in FIG. 8c, may be used. An exemplary single lumen catheter is a conventional multipurpose catheter. Such conventional catheter assemblies are available from Cordis Corporation, located in Miami, Fla.

The y-connector 214 is conventional. An exemplary y-connector 214 is depicted in FIG. 6 and comprises a connector 252 located at the distal end 216 of the y-connector 214, a shaft 254 having a side arm 228, and a Tuohy-Borst connector 256 located at the proximal end 220 of the y-connector 214. The Tuohy-Borst connector 256 has a rotatable hub 258 with a threaded hemostatic valve member (not shown) that carries an O-ring (not shown). Such y-connectors are available from Devices for Vascular Intervention, Inc., located in Temecula, Calif.

The connector assembly 218 is also conventional. The connector assembly 218 comprises a male luer lock connector 260 located at the distal end 262 of the connector assembly 218 and a female luer lock connector 264 located at the distal end 224 of the connector assembly 218. A typical supplier of the connector assembly 210 is NAMIC, Inc., located in Glens Falls, N.Y.

Figure 9:
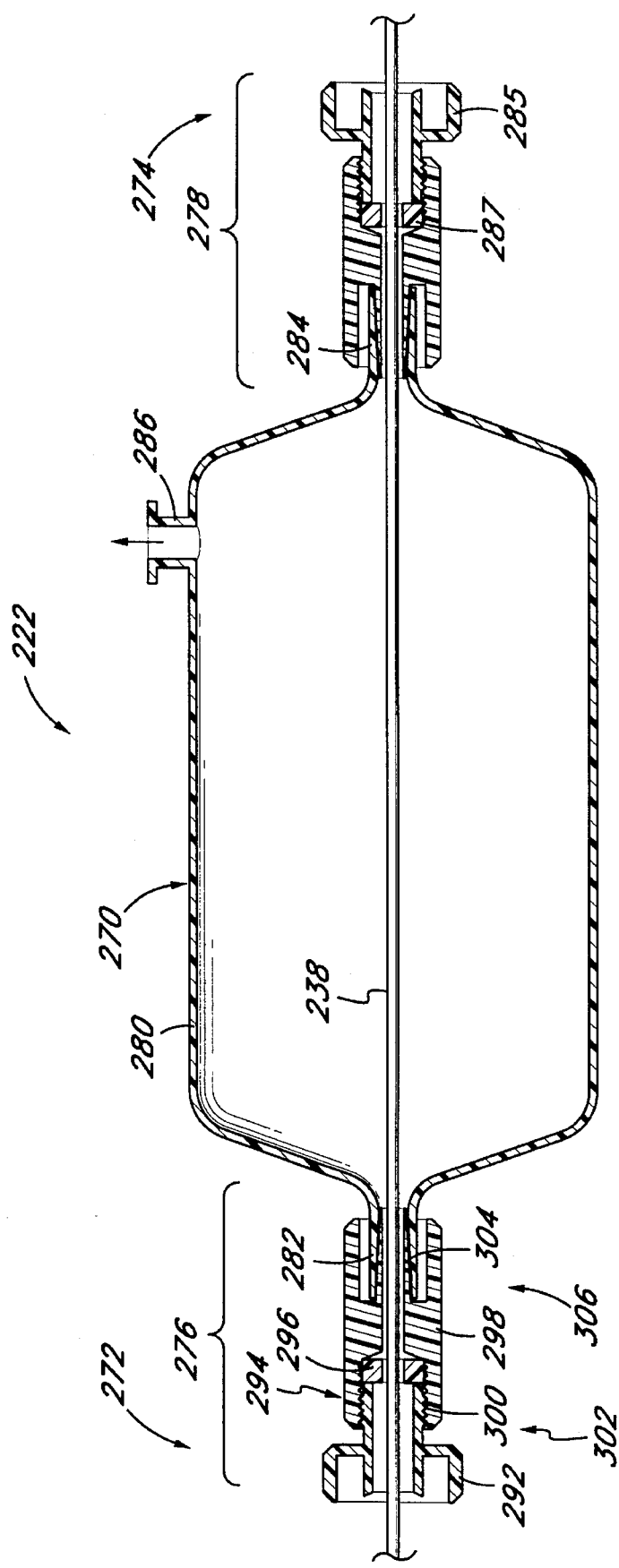
FIG. 9 illustrates an enlarged, cross-section view of the evacuation chamber used in a preferred embodiment of the aspiration assembly of FIG. 6.

As illustrated in FIGS. 6 and 9, the evacuation module 222 comprises an evacuation chamber 270 having a distal end 272 and a proximal end 274, a first Tuohy-Borst connector 276 located at the distal end 272 of the evacuation chamber 270 and a second Tuohy-Borst connector 278 located at the proximal end 274 of the evacuation chamber 270.

With reference to FIG. 9, the evacuation chamber 270 comprises a generally tubular body 280, which tapers into a first and a second tubular member 282, 284 at the distal end 272 and the proximal end 274 respectively. The tubular body 280 of the evacuation chamber 270 is also provided with a port 286. In a preferred embodiment, the port 286 (see FIG. 6) is connected to a suction tubing 288, which is in turn connected to a vacuum bottle adapter 290. The guidewire is withdrawn proximally from the improved aspirator assembly 210 and the Tuohy-Borst connector 278 is sealed. Sealing of the Tuohy-Borst connector 278 is accomplished by rotating the rotatable hub 285 clockwise, resulting in the exertion of pressure on the O-ring 287. This pressure causes elastic deformation of the O-ring 287, resulting in the closing of the aperture of the O-ring 287. The rotatable hub 285 is rotated until the O-ring 287 seals completely. The vacuum bottle adapter 290 is then coupled to a vacuum bottle (not shown) for aspiration purposes. The suction tubing 288, vacuum bottle adapter 290 and vacuum bottle are commercially available from Inter Ventional Technologies Inc. in San Diego, Calif. and Advanced Cardiovascular Systems, Inc. in Temecula, Calif. Alternatively, the port 286 may be connected to any vacuum source or a suction member such as a syringe (not shown).

The Tuohy-Borst connectors 276 and 278 are substantially identical. For discussion purposes, reference will only be made to connector 276. The Tuohy-Borst connector 276 comprises a rotatable hub 292 with a threaded hemostatic valve member 294 located adjacent to an O-ring 296. The Tuohy-Borst connector 276 further comprises a sheath 298 having internal threads 300 on a first end 302 and a male connector 304 on a second end 306. A typical supplier of the Tuohy-Borst connector 276 or 278 is United States Catheter Incorporated (USCI), located in Billerica, Mass.

Figure 10:
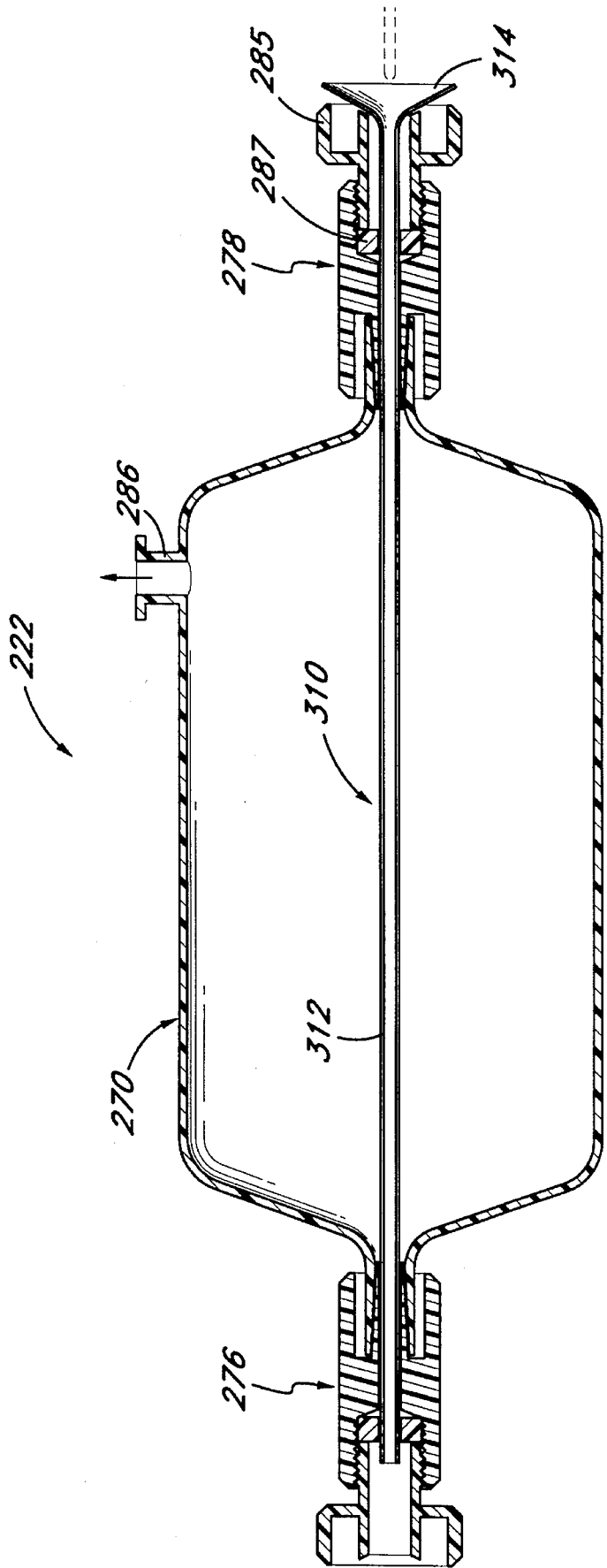
FIG. 10 illustrates a cross-section view of an introducing stylet within the evacuation chamber of FIG. 9.

As depicted in FIG. 10, an additional component of the present invention is an introducing stylet 310. In a preferred embodiment, the stylet 310 comprises a hollow tube 312 which extends into a funnel 314 at one end. The introducing stylet 310 is inserted into the evacuation chamber 270 via the Tuohy-Borst connector 278 upon removal of the guidewire 238, as discussed in greater detail below. The styler 310 should be of a sufficient axial length so as to substantially traverse the length of the evacuation chamber 270. Suppliers of such stylers include Advanced Cardiovascular Systems, Inc. located in Temecula, Calif. and United States Catheter Incorporated (USCI), located in Billerica, Mass. In an alternate embodiment, a dilator may be used. A typical supplier of such dilators is Daig Corporation of Minnetonka, Minneapolis. The use of the stylet 310 facilitates the introduction of guidewires or infusion wires into the evacuation chamber 222, as will be discussed in detail below. When aspiration is required, the stylet 310 is withdrawn proximally and the Tuohy-Borst connector 278 is sealed as described above. The port 286 is then connected to a vacuum source or a suction member, which will then be activated for aspiration purposes.

With reference to FIG. 7 and as earlier described, the infusion assembly 226 comprises a connector assembly 227 connected to a side arm 228 of the y-connector 214, a manifold 230 connected to the connector assembly 227 at a distal end 232 of the manifold 230 and a syringe 234 connected to the proximal end 235 of the manifold 230.

The connector assembly 227 is conventional, and comprises a connecting line 320, a first male luer lock connector 322 at its distal end 324, and a second male luer lock connector 326 at its proximal end 328. Such connector assemblies may be obtained from the Namic Angiographic Systems Division in Glens Falls, N.Y.

The manifold 230 is also conventional. An exemplary manifold 230 is depicted in FIG. 7 and comprises a tubular member 340 with a hub 342 mounted over one end 232 of the tubular member 340, and three T-connectors 344, 346, 348, forming inlets or outlets located along the body of the tubular member 340. Associated with each T-connector 344, 46, 348 is a control valve 350, 352, 354. The hub 342 is freely rotatable around the longitudinal axis of the tubular member 340 and has internal threads (not shown) for engaging male connector 326. Typical suppliers of the manifold include Merit Inc., which is located in Salt Lake City, Utah and Namic, which is located in Albany, N.Y.

As described earlier, various fluids may be introduced through each T-connector 344, 346, 348, of the manifold 230. Some fluids used are: saline, which is used for flushing the catheter 236; a radiopaque contrast agent, which is used to determine the patency of the vessel or chamber under fluoroscopic examination, or for providing fluoroscopic guidance of the catheterization process; or any medication required. A control valve 350, 352, 354 connected to each T-connector 344, 346, 348 is used to regulate the amount of fluid required. In one embodiment, one of the T-connectors 344, 346, or 348 is connected to a source of vacuum.

In the present embodiment, a conventional syringe 234 is connected to the manifold 230, at the proximal end 235 of the manifold 230. The syringe 234 comprises a generally tubular body 360 and a plunger 362. Markings 364 indicating the fluid capacity of the syringe 234 are located on the exterior wall of the tubular member 360. The syringe 234 is commercially available from Namic, located in Albany, N.Y. In an alternate embodiment, a vacuum reservoir (not shown) may be used in place of the syringe 234. Such vacuum reservoirs may take the form of vacuum bottles, which are known in the art. These vacuum bottles are available from Inter Ventional Technologies, Inc. of San Diego, Calif.

In addition, a pressure monitoring system (not shown) may be connected to the manifold 230 at one of the T-connectors 344, 346, or 348, as known in the art. The pressure monitoring system is used to monitor pressure within the cardiac chambers and large vessels during catheterization, and it provides important information regarding hemodynamics, such as the rate of blood flow and amount of pressure within blood vessels and the heart chambers. In operation, the catheter assembly 212, the y-connector 214, the connector assembly 218, the evacuation module 222, the connector assembly 227, the manifold 230 and the syringe 234 are all in fluid communication with one other. The present apparatus also provides the clinician with the option of terminating fluid communication between these components of the improved aspirator assembly 210 either at the proximal end 220 of the y-connector 214, the distal end 272 of the evacuation module 222 or the proximal end 274 of the evacuation module 222.

Figure 11A:
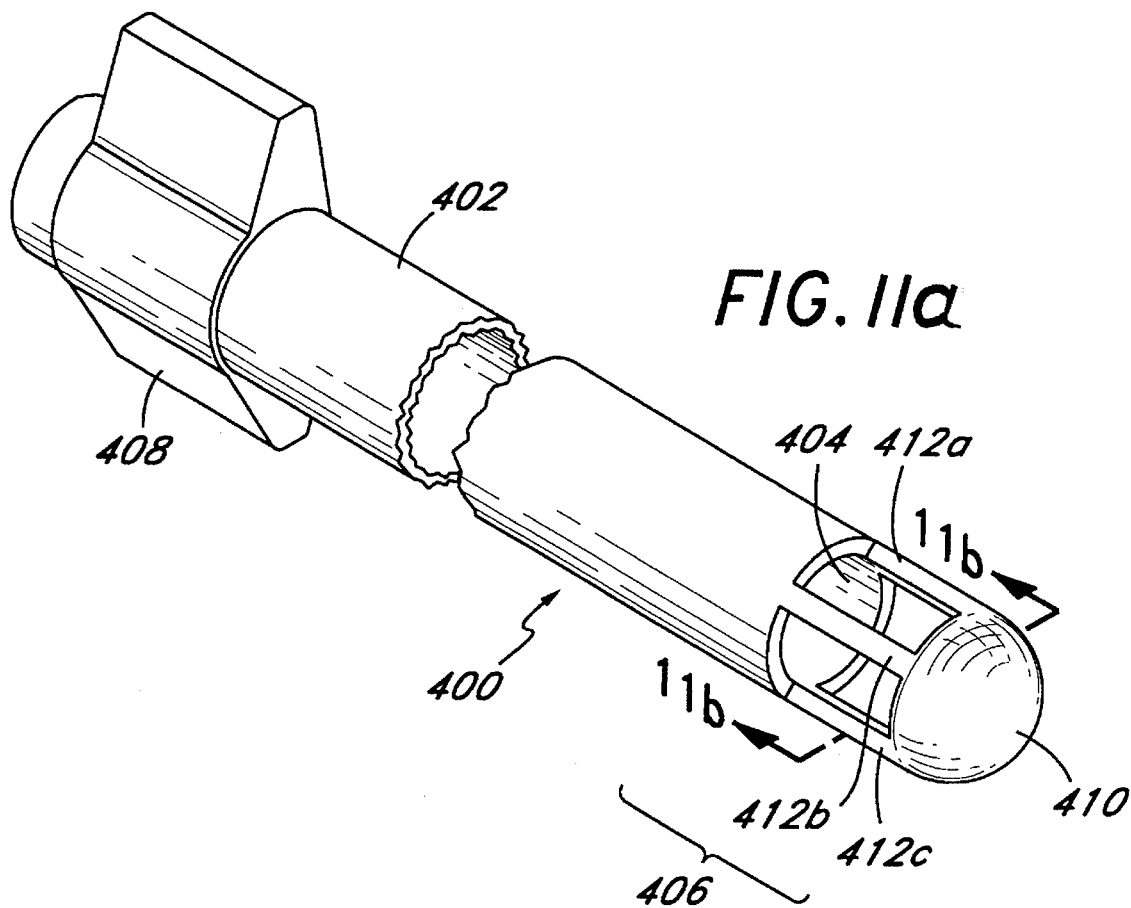
FIG. 11a is a perspective view of a preferred embodiment of the infusion wire of the present invention.
Figure 11B:
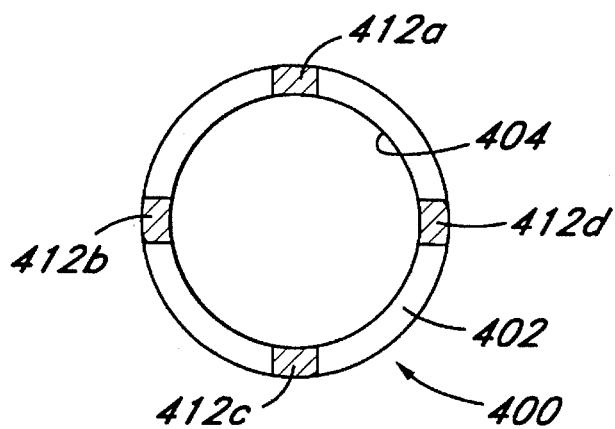

A further aspect of the present invention is an infusion wire which facilitates drug delivery to the treatment site and/or pulverization of occlusions at the treatment site. As illustrated in FIGS. 11a and 11b, the infusion wire 400 comprises a generally tubular body 402 with a central lumen 404, a distal tip 406 and a connector 408 at its proximal end. The tip 406 comprises a cap 410 and four struts 412a–d which extend from the distal end of the tubular body 402. The tip 406 may comprise fewer than or more than the four struts 412a–d, as is apparent to one skilled in the art. Preferably, each strut is between 1.0 to 2.0 mm long. In a preferred embodiment, the cap is conical. In an alternate embodiment, the cap is hemispherical.

Figure 12A:
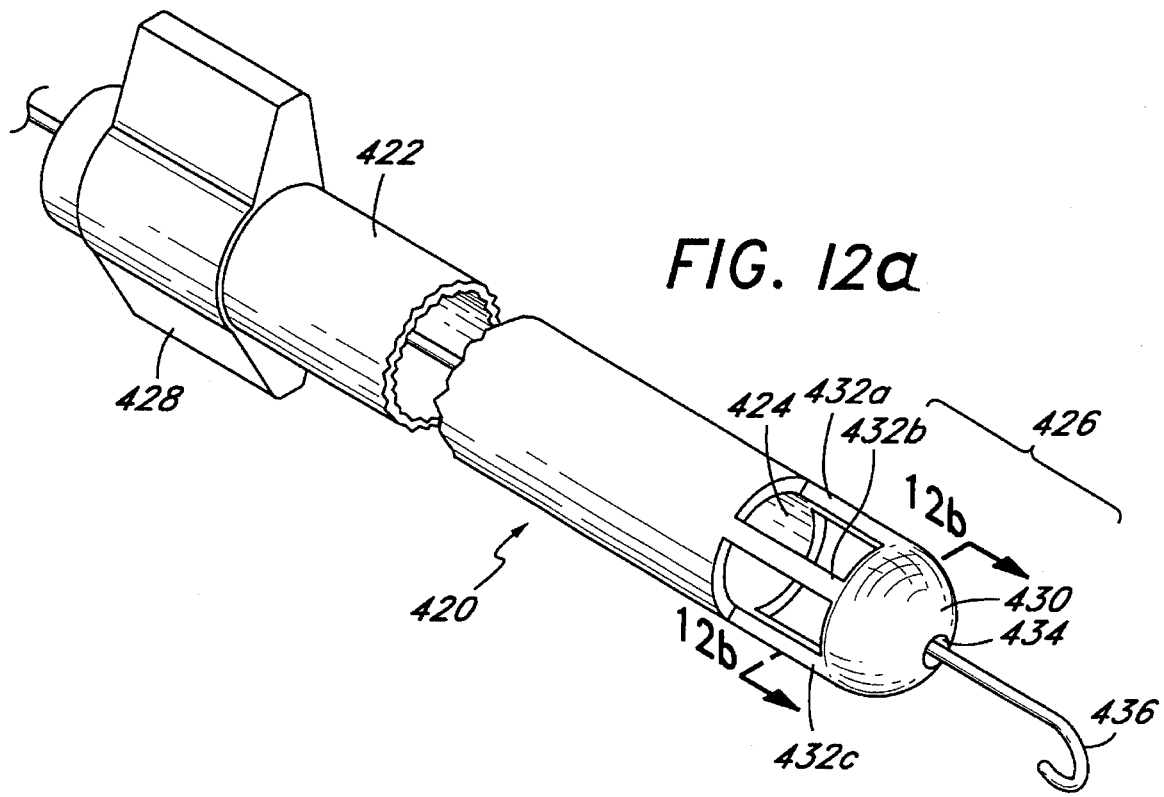
FIG. 12a illustrates an alternate embodiment of the infusion wire of the present invention.
Figure 12B:
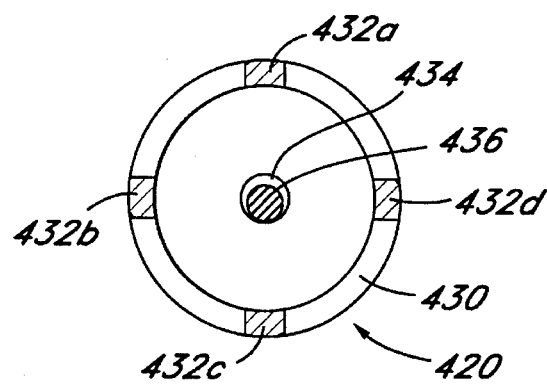

FIGS. 12a and 12b illustrate a further embodiment of the infusion wire of the present invention. In this embodiment, the infusion wire 420 comprises a generally tubular body 422 with a central lumen 424, a distal tip 426 and a connector 428 at its proximal end. The tip 426 comprises a cap 430 and four struts 432a–d which extend from the distal end of the tubular body 422. The cap 430 defines a substantially central aperture 434 located approximately at the apex of the cap 430. In a preferred embodiment, the cap is conical. In an alternate embodiment, the cap is hemispherical. Preferably, the central aperture 434 has a cross-section of between about 0.016 to 0.022 inches. The tip 426 may comprise fewer than or more than the four struts 432a–d, as is apparent to one skilled in the art. Preferably, each strut is between approximately 1.0 to 2.0 mm long.

The infusion wire 420 further comprises a fine guidewire 436 which is first inserted through the central lumen 424 of the infusion wire 420 and then through the central aperture 434. The infusion wire 420 and the guidewire 436 may be used to advance to finer blood vessels which cannot accommodate the catheter 236 earlier described. The guidewire wire 436 is commercially available in a variety of sizes and with a variety of tips. Preferably, a guidewire 436 with a diameter of between 0.014 to 0.021 and with a J-shaped or straight tip is used. Such guidewires are available from SCIMED in Minneapolis, Minn. and Advanced Cardiovascular Systems, Inc. located in Temecula, Calif.

Preferably, the infusion wire 400 or 420 is made of a material which is sufficiently strong to withstand the outwardly radiating forces exerted by fluids travelling through the wire. In addition, the wall of the infusion wire 400 or 420 should be of a sufficiently thin construction so that lumen 404 or 424 will be provided with the largest possible cross-section. This feature ensures that the delivery of medication or aspiration of occlusions is facilitated. The infusion wire 400 or 420 is preferably also made from materials which have at least a biocompatible exterior surface. In one embodiment, the tubular body 402 of the infusion wire 400 or tubular body 422 of the infusion wire 420 is made from Teflon-coated stainless steel. In an alternate embodiment, the tubular body 402 or 422 is made from coiled or braided stainless steel wires, as known in the art.

The inner walls of infusion wire 400 oe 420 thus constructed is coated with a suitable material, as discussed below.

As in the case of the catheter 236, biocompatibility can be enhanced by applying any of a variety of coatings to the exterior wall of the infusion wire 400 or 420. In addition, other coatings which inhibit thrombus formation or which provide a smooth surface, may be applied, as is understood by one of skill in the art. The provision of a smooth coating on the exterior surface of the infusion wire 400 or 420 serves, in part, to prevent scarring of the intravascular walls as the infusion wire 400 is advanced into the intravascular system. In addition, where the infusion wire 400 or 420 is made from coiled or braided wires, a coating is required to ensure that the walls of the infusion wire 400 or 420 are impervious to fluids. Examples of coatings which exhibit such a property include polyethylene and PET.

In a preferred embodiment, both the interior and exterior surfaces of the infusion wire 400 or 420 are coated to impart the properties discussed above. Alternatively, only the interior or exterior surface of the infusion wire 400 or 420 alone could be coated, or multiple coats of the same or different material could be used on the interior or exterior surface of the infusion wire 400 or 420.

Suitable coating materials such as polyethylene or PET or other materials that can be readily selected by one of skill in the art. In general, any biocompatible material which can tolerate the forces exerted by the fluids travelling through the wire 400 or 420 can be used. However, a non-biocompatible material may be used as one of multiple coatings where the non-biocompatible material is sandwiched between other layers, such that the material is not exposed to body tissues.

Coating material may be applied to individual surfaces by painting, bonding with a suitable adhesive or mechanically fixing as appropriate to the material of the coating and material comprising the bulk of the catheter body as will be appreciated by one with skill in the art. Alternatively, internal and external coatings may be applied by inserting the infusion wire 400 or 420 into an envelope of suitable material as is discussed above.

The wall thickness of the infusion wire 400 or 420 will vary depending on the required application. Typically, the wall thickness of an infusion wire made of Teflon-coated stainless steel is preferably between about 0.010 and 0.025 inches. More preferably, the infusion wire has a wall thickness of between about 0.015 and 0.02 inches. In some cases a wall thickness of less than about 0.010 inches may be desired. In addition, some instances may require a wall thickness of greater than about 0.025 inches.

Like the catheter 236, the wall thickness of the infusion wire 400 or 420 will generally be substantially uniform throughout the axial length of the infusion wire 400 or 420. However, the wall thickness on the proximal end of the infusion wire 400 or 420 may be different from the wall thickness on the medial or distal portion of the infusion wire 400 or 420, such as in the case where bonding to the connector 408 or 428 is required, so that the strength profile of the bonding may be increased.

The outer diameter, inner diameter and axial length of the infusion wire 400 or 420 will vary with the specific intended application. One skilled in the art will be readily able to choose the appropriate insertion diameter of the infusion wire 400 or 420 depending on the diameter of the catheter through which the infusion wire will be inserted.

Preferably, the infusion wire 400 or 420 has an outer diameter of between about 0.035 inches and 0.038 inches for an infusion wire 400 made of stainless steel. The infusion wire 400 or 420 should also preferably have an inner diameter of between about 0.032 to 0.034 inches. Both ideal outer diameter and ideal wall thickness will be determined by the inherent strength of the material used as will be apparent to one skilled in the art. Therefore, the dimensions given herein should be considered exemplary.

Furthermore, the clinician should select an infusion wire 400 or 420 having an axial length that will be sufficiently long to traverse to the treatment site. The axial length of the infusion wire 400 or 420 for intravascular, pulmonary and cardiac applications will typically be in the range from about 55 inches to 65 inches. The axial length may vary considerably from case to case depending upon the application to different parts of the anatomy.

In use and as illustrated in FIG. 3, access to the intravascular system or heart chambers is generally gained through the right or left femoral artery (not shown) or vein 80, 82, as described earlier. Access may also be gained through the brachial vessels 84, 86 in the right and left arms. Once access into the intravascular system is accomplished, the catheter assembly 212 is advanced into the femoral vein 80 or 82 with the connector 242 of the catheter assembly 212 remaining outside the vein 80 or 82.

To reach the pulmonary arteries, the catheter assembly 212 is advanced under pressure monitoring and/or fluoroscopic guidance, through the right or left common iliac 96 or 98 and the inferior vena cava 100, into the right atrium 102. The catheter assembly 212 is then advanced through the tricuspid valve (not shown) into the right ventricle 104, up the pulmonary trunk 106, and henceforth into the right or left main pulmonary artery 88 or 90. Once the catheter assembly 212 reaches the pulmonary trunk 106, or the cardiac chambers 102,104, a radiopaque contrast agent may be injected through the connector 242 of the catheter 236, to facilitate fluoroscopic guidance of the catheter assembly 212 into the pulmonary artery 88 or 90. Typical contrast agents used include ionic contrast agents such as Renograffin or MD 76, or nonionic contrast agents such as Optiray or Hexabrix. Renograffin is commercially available through Bristol-Myers Squibb Diagnostics in Princeton, N.J. MD 76, Optiray and Hexabrix are all commercially available from Mallinckrodt Incorporated in St. Louis, Mo.

Selective injection of the radiographic contrast agent into the cardiac chambers 102, 104, pulmonary trunk 106 or pulmonary vessels 88, 90, 108, 110 facilitates contrast radiographic inspection of the vessel, which in turn permits the placement of the catheter assembly 212 into the intravascular site of interest. A contrast agent is also injected into the site under examination during recording of radiographic images. Each vessel is usually viewed in several projections, to permit assessment of severity of stenosis or occlusive emboli and to minimize overlap of adjacent vessels. Injecting the contrast agent into the pulmonary system also facilitates the location of occlusions such as clots in the pulmonary vessels 108, 110.

Under fluoroscopic guidance, the catheter assembly 212 is advanced to the occluded pulmonary artery. At this juncture, the guidewire 238 may be withdrawn from the catheter assembly 212. Upon removal of the guidewire 238, the stylet 310 is introduced into the evacuation module 222 via the Tuohy-Borst connector 278, as shown in FIG. 10. With the styler 310 in place, the infusion wire 400 is introduced into the evacuation module 222, and advanced through the connector assembly 218, the y-connector 214, through the first lumen 244 of the catheter 240 until the tip 406 of the wire 400 reaches the treatment site. The stylet 310 is then withdrawn proximally from the evacuation module 222. The hub of the Tuohy-Borst connector 278 is next tightened to ensure that the infusion wire 400 extending through the aspirator assembly 210 is held in place and to provide a complete seal at the proximal end 274 of the evacuation module 222. Care is taken to ensure that the valve members within the Tuohy-Borst connectors 256 and 276 are open so that fluid communication between the catheter 236, the y-connector 256, the connector asembly 218 and the evacuation chamber 270 is maintained. With the infusion wire 400 in place, treatment of the intravascular site in accordance with the present invention begins.

Figure 13:
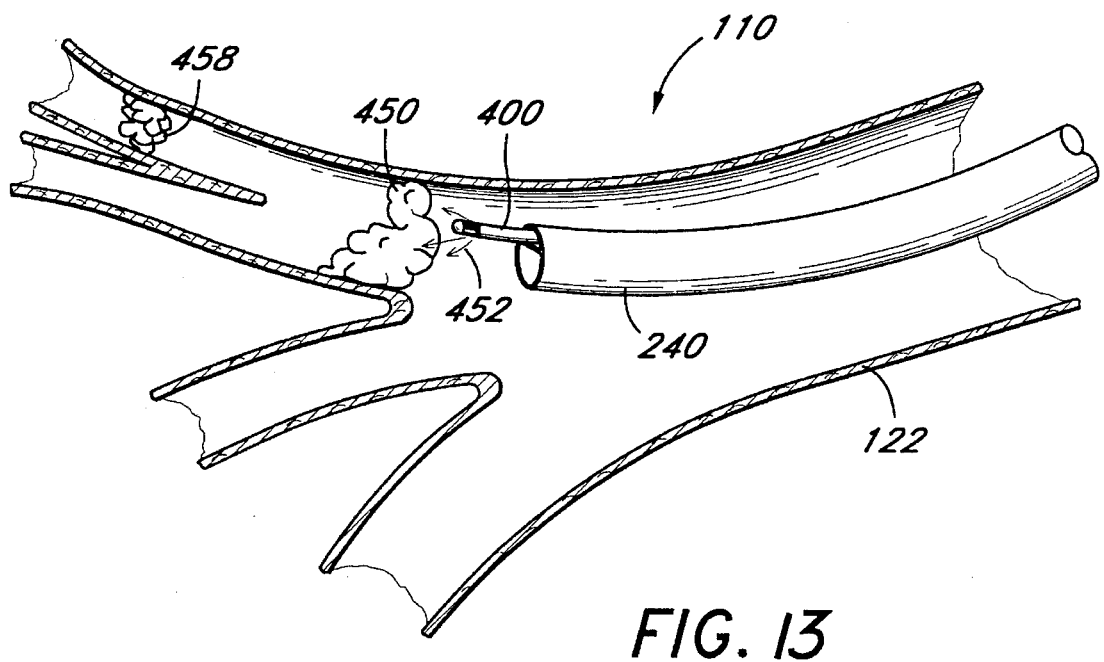
FIG. 13 illustrates an enlarged view of the improved catheter of FIG. 8a and the infusion wire of FIGS. 11a and 11b used to infuse medication and pulverize occlusions at the treatment site.

As illustrated in FIG. 13, the elongated tube portion 240 of catheter 236, and the tip 406 of the infusion wire 400 are positioned close to the occlusion 450 in the pulmonary vessel 122 once the position of the occlusion 120 is determined. In the present embodiment, a thrombolytic agent is administered to the occlusion 450, through the infusion wire 400 as depicted by arrows 452 through the tubular member 402 of the infusion wire 400.

An anticoagulation agent such as Heparin may also be administered to the occlusion 450 to minimize coagulation of the occlusion 450 when it is fragmented. Heparin is commercially available through The Upjohn Company in Kalamazoo, Mich.

Figure 14:
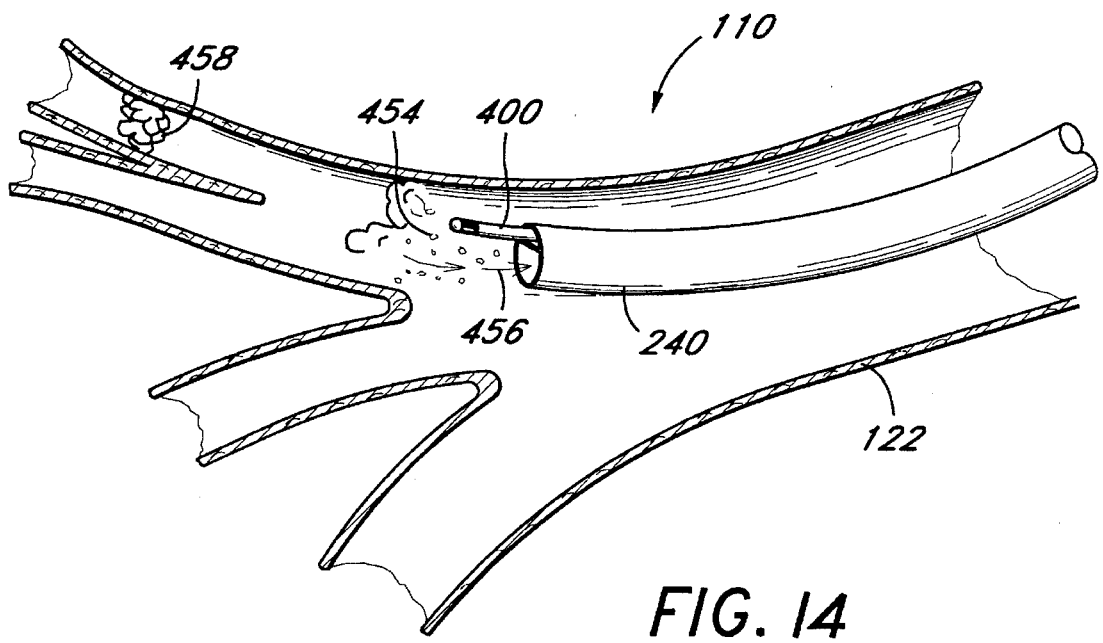
FIG. 14 illustrates the improved catheter of FIG. 13 being used to aspirate occluding substances within a blood vessel.

If the thrombolytic agent acts sufficiently to break the occlusion 450 into small enough pieces, the residue 454 of the occlusion 450 is aspirated immediately through the second lumen 246 of the catheter 240 by activating the vacuum source (not shown) connected to the port 286 of the evacuation chamber 270, as indicated by the arrows 456 shown in FIG. 14.

Alternatively, the Tuohy-Borst connector 256 of the y-connector 214 may be sealed and the occlusions may be aspirated by drawing the plunger 362 of the syringe 234 backwards, which creates a pressure difference within the tubular body 364 of the syringe 234. This pressure difference acts almost instantaneously to draw the residue 456 of the occlusion 450 into the syringe 234. Typically, a 50 cc syringe would be sufficient for this purpose. In an alternate embodiment, a vacuum reservoir (not shown) may be used in place of the syringe. The vacuum reservoir may be connected to the manifold 230 at one of the T-connectors 344, 346, or 348, or at the proximal end 235 of the manifold 230. An exemplary vacuum reservoir is a vacuum bottle. This procedure may be repeated as needed. When the occlusion 450 or its residue 454 has been removed, the distal end of the catheter 236 may be advanced under fluoroscopic guidance to vessels downstream, so that occlusions 458 further downstream may be similarly removed.

However, if the thrombolytic agent does not break the occlusion 450 into sufficiently small pieces for immediate aspiration through the catheter 236, the infusion wire 400 may be used to manually pulverize the occlusion 450 or its residual pieces 454 into particles small enough to be aspirated, as shown in FIG. 14. A thrombolytic agent may be administered via one of the T-connectors 344, 346 or 348 through the second lumen 246 of the catheter 240 simultaneously.

Figure 15:
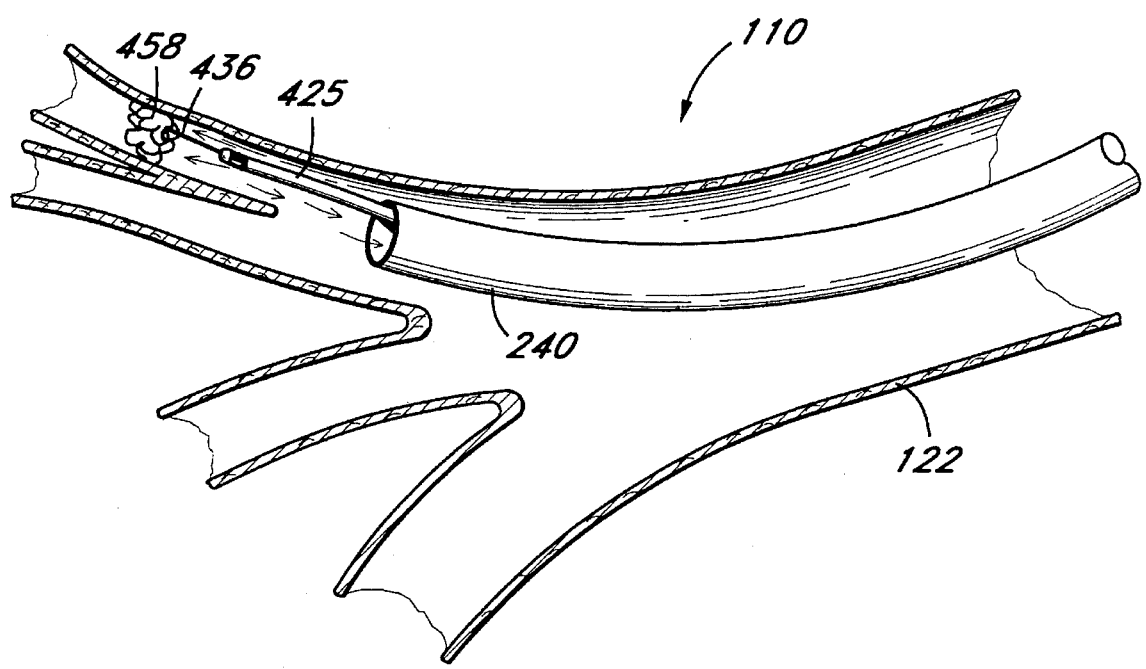
FIG. 15 illustrates the improved catheter of FIG. 7 and the infusion wire of FIGS. 12a and 12b in use at the treatment site.

When the residue 454 has been pulverized into particles small enough to pass through the second lumen 246 of the catheter 236, the vacuum source connected to the port 286 of the evacuation chamber 270 is activated, drawing the residue 454 of the occlusion 450 into the evacuation chamber 270.

Where occlusions 458 are located in vessels too fine to accommodate the catheter 236, the clinician may withdraw the infusion wire 400 from the improved aspirator assembly 210 and introduce the infusion wire 420, along with the fine guidewire 436 into the improved aspirator assembly 210. When the infusion wire 420 and the guidewire 436 have been advanced to the vicinity of the occlusion 458, as illustrated in FIG. 15, treatment in accordance with the method of the present invention may begin. The pressure within the patient's heart chambers or vessels is monitored throughout the above described procedure. When contrast radiographic inspection indicates that there is no evidence of any remaining residual occlusions 454, the catheter 236 together with the infusion wire 400 or 420 and guidewire 436 (if used) is withdrawn.

It should be noted that any occlusion within a vessel or any heart chamber may be aspirated in the manner described above without first administering thrombolytic agents if the occlusions are small enough to be aspirated. The above described procedure can be performed in any part of the intravascular, pulmonary or coronary system, or within the chambers of the heart.

In practice, the present invention allows the removal of occlusions, thereby restoring vascular competence. Use of the improved aspirator assembly 210 in the method of the present invention provides several advantages over the use of conventional apparatus. First, the provision of two lumens in the catheter 212 permits the simultaneous delivery of medication and the aspiration of occlusions. This feature of the catheter design, in conjunction with the use of the infusion wire, also permits the pulverization of occlusions while facilitating the delivery of medication and the aspiration of occlusions. Second, the improved aspirator assembly does not require any disassembly in the course of administrating the method of the present invention. This is a significant advantage since delay increases the risk of morbidity and mortality. Third, the improved aspirator assembly provides at least two means of aspirating occlusions: (i) the evacuation chamber and (ii) the syringe or an equivalent suction member. In the event that one vacuum source of suction member fails, a back-up system is immediately available. Fourth, the infusion wire not only facilitates the delivery of medication but also provides a tip that is sufficiently rigid for pulverizing occlusions. Finally, the use of the infusion wire 420 and the fine guidewire 436 allows the method of the present invention to be performed in blood vessels too fine to accommodate the catheter 236.

Although the present invention has been described in terms of certain preferred embodiments, other embodiments can be readily devised by one skilled in the art in view of the foregoing. Accordingly, the scope of the present invention is defined by reference to the appended claims.

What is claimed is:

1. A method of removing free emboli from an intravascular site, comprising:
    advancing a catheter having a distal end and a proximal end through a patient's vasculature until said distal end of said catheter extends into an area adjacent said site while said proximal end remains outside of said patient;
    introducing a medication through said proximal end of said catheter to discharge said medication through said distal end of said catheter; and
    aspirating said free emboli through said distal end of said catheter and out said proximal end of said catheter without breaking up said free emboli.

2. A method as in claim 1, further including the steps of advancing a guidewire into said patient's vasculature to said site, such that a portion of said guidewire remains outside said patient; and advancing said catheter over said portion of said guidewire remaining outside said patient prior to advancing said catheter through said patient's vasculature.

3. A method as in claim 1, wherein said medication is a thrombolytic agent or an anticoagulant.

4. A method of removing occlusions from an intravascular site, comprising:
   advancing a catheter assembly through a patient's vasculature until a distal end of said catheter assembly is adjacent said site, said catheter assembly comprising:
      a guidewire having a predetermined diameter, and a distal tip, and
      a catheter having an elongated tubular body, said catheter being
   positioned over said guidewire;
   pulverizing said occlusions using said distal tip of said guidewire to contact said occlusions; and
   aspirating said occlusions through said catheter.

5. An apparatus for removing intravascular occlusions, comprising:
   a catheter having an elongated tubular body, said tubular body having at least a first lumen extending therethrough, a proximal end and a distal end;
   an infusion guide wire for insertion through said first lumen comprising:
      an elongated tubular body;
      a proximal end and a distal end adapted to pulverize said occlusions by contacting said occlusions; and
   a suction member coupled to said proximal and of said catheter for aspirating said occlusions through said elongated tubular body of said catheter.

6. The apparatus of claim 5, further comprising a second guidewire positioned within said infusion wire and having a distal tip extending through an opening located in said distal end of said infusion wire and shaped to pulverize said occlusions.

7. A method of removing intravascular occlusions, comprising:
   advancing a catheter assembly through a patient's vasculature until a distal end of said catheter assembly extends into an area adjacent said occlusions, said catheter assembly comprising:
      a catheter having an elongated tubular body, and a first lumen and a second lumen extending therethrough, a proximal end and a distal end; and
      a guidewire inserted within said first lumen or said second lumen, for directing said catheter to said area adjacent said occlusions; and
   aspirating said occlusions through said first lumen or said second lumen and out said distal end of said catheter.

8. The method of claim 7, further comprising the step of discharging a thrombolytic agent or anti-coagulant through said first lumen or said second lumen of said catheter, prior to aspirating said occlusions.

9. A method of removing occlusions from an intravascular site, comprising:
   advancing a guidewire through a patient's vasculature until a distal end of said guidewire is adjacent said occlusions;
   advancing a hollow catheter over said guidewire until a distal end of said catheter is adjacent said site,
   removing said guidewire from said catheter;
   advancing an infusion wire comprising an elongated tubular body, a proximal end, and a distal tip into said hollow catheter until the distal tip of said infusion wire is adjacent said site;
   introducing a medication through said proximal end of said infusion wire to discharge said medication through said distal tip of said infusion wire; and
   aspirating said occlusions through said distal end of said catheter, said first lumen or said second lumen of said catheter, and out said proximal end of said catheter without breaking up said occlusions.

10. An apparatus for removing intravascular occlusions, comprising:
    a catheter having an elongate tubular body, a proximal end and a distal end, said tubular body having at least a first lumen extending therethrough; and
    a guidewire insertable through said lumen having a distal end shaped to pulverize said occlusions by contact with said occlusions.

11. The apparatus of claim 10, further comprising a suction member connected to said proximal end of said catheter for aspirating said occlusions through said catheter.

12. The apparatus of claim 11, wherein said suction member is a syringe.

13. The apparatus of claim 11, wherein said suction member is a vacuum reservoir.

* * * * *

UNITED STATES PATENT AND TRADEMARK OFFICE
CERTIFICATE OF CORRECTION

PATENT NO.         : 5,476,450                                              Page 1 of 1
APPLICATION NO. : 08/177852
DATED              : December 19, 1995
INVENTOR(S)        : Joseph M. Ruggio It is certified that error appears in the above-identified patent and that said Letters Patent is hereby corrected as shown below:

In Claim 7, Column 20, Line 6, please change "... second lumen and out said distal end of said catheter.," to read --... second lumen and out said proximal end of said catheter without breaking up said occlusions.--

Signed and Sealed this

First Day of May, 2007

JON W. DUDAS
*Director of the United States Patent and Trademark Office*